United States Patent
Tang et al.

(10) Patent No.: US 9,511,057 B2
(45) Date of Patent: Dec. 6, 2016

(54) METHODS FOR TREATING DENERVATION-INDUCED MUSCLE ATROPHY

(71) Applicants: Huibin Tang, Palo Alto, CA (US); Joseph Shrager, Stanford, CA (US)

(72) Inventors: Huibin Tang, Palo Alto, CA (US); Joseph Shrager, Stanford, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 41 days.

(21) Appl. No.: 14/213,141

(22) Filed: Mar. 14, 2014

(65) Prior Publication Data

US 2014/0275228 A1    Sep. 18, 2014

Related U.S. Application Data

(60) Provisional application No. 61/791,249, filed on Mar. 15, 2013.

(51) Int. Cl.
*A61K 31/436* (2006.01)
*C07K 14/47* (2006.01)

(52) U.S. Cl.
CPC ................ *A61K 31/436* (2013.01)

(58) Field of Classification Search
USPC .......... 435/6.1, 91.1, 9, 1.31, 455, 69.1, 1.1, 435/325, 45, 5, 375; 514/1, 2, 44, 291; 536/23.1, 24.5; 424/9, 9.1; 530/350
See application file for complete search history.

(56) References Cited

U.S. PATENT DOCUMENTS

2014/0302023 A1* 10/2014 Frenette ............ A61K 31/7105
424/133.1

OTHER PUBLICATIONS

Bentzinger et al, Cell Metabolism, vol. 8, pp. 411-424 (2008).*
Risson et al, J. Cell.Biol., vol. 187, No. 6, pp. 859-874 (2009).*

* cited by examiner

*Primary Examiner* — Jane Zara
(74) *Attorney, Agent, or Firm* — Stanford University; Andrea Blecken

(57) ABSTRACT

The present invention provides methods for the treatment of denervation-induced skeletal muscle atrophy, and generally, denervation-induced skeletal muscle degeneration diseases using agents that decrease the activity of mammalian target of rapamycin and/or the activity of at least one of the Forkhead Box Transcription Factors 1, 3 and 4.

11 Claims, 8 Drawing Sheets

Figure 4A-G
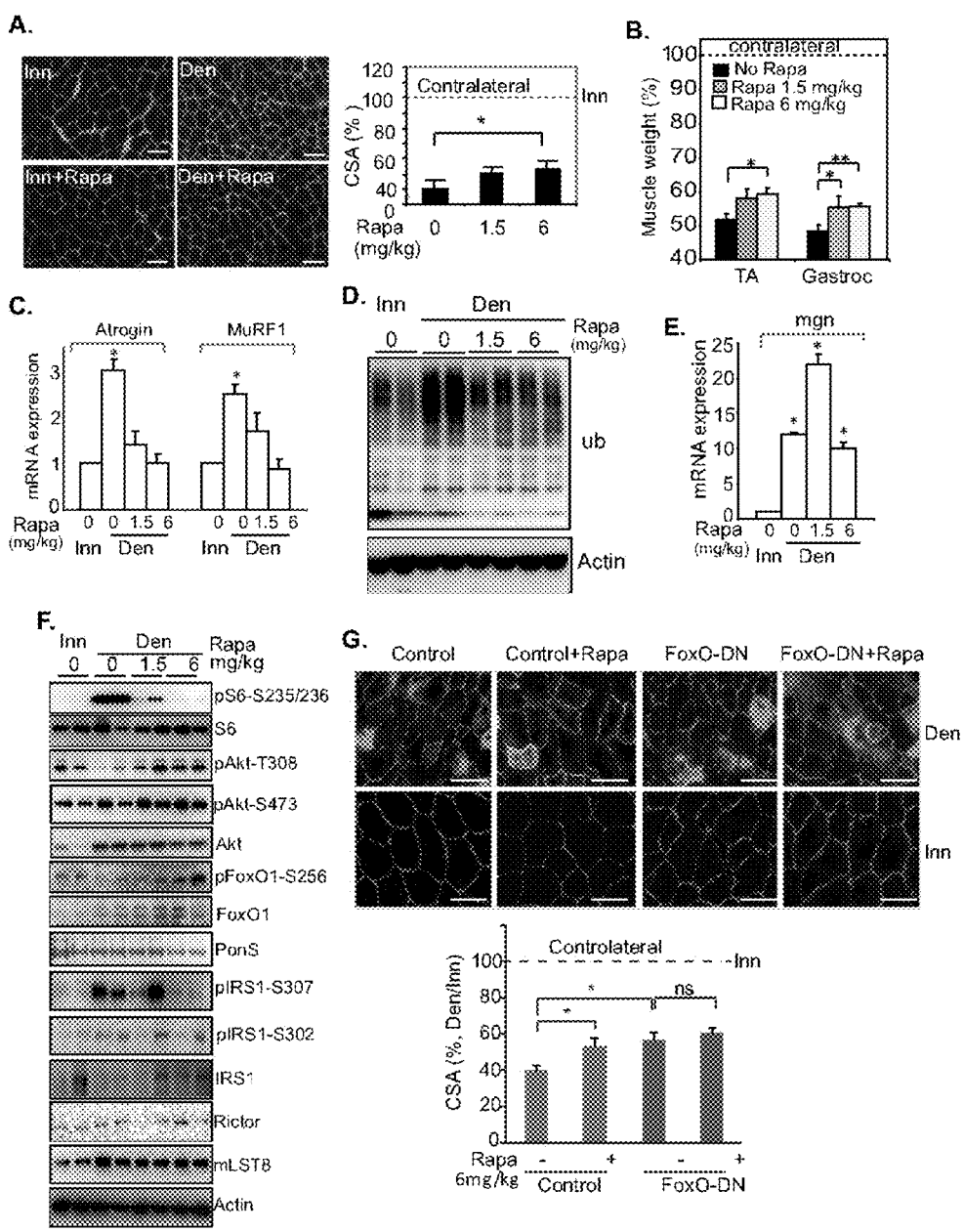

Figure 4H-J
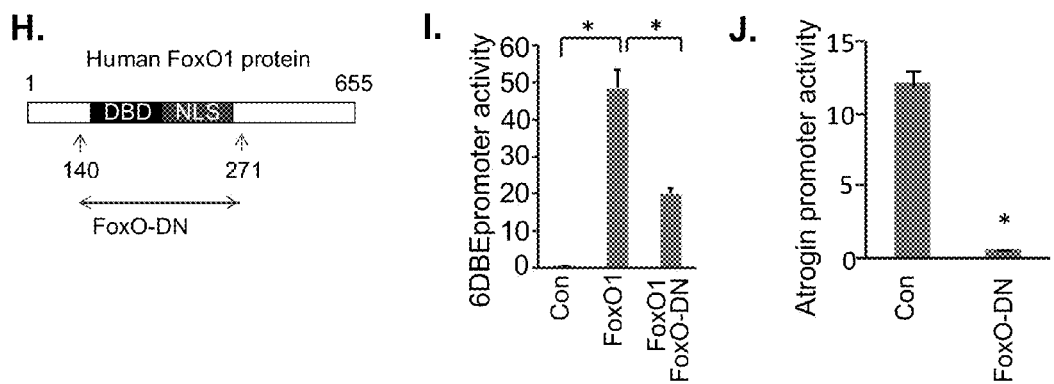

Figure 6

SEQ ID NO: 1  TAT  FoxO-DN

TAC GGT CGT AAA AAA CGT CGT CAG CGT CGT CGT GCC GCC GCT GGG
CCG CTC GCG GGG CAG CCG CGC AAG AGC AGC TCG TCC CGC CGC AAC
GCG TGG GGC AAC CTG TCC TAC GCC GAC CTC ATC ACC AAG GCC ATC
GAG AGC TCG GCG GAG AAG CGG CTC ACG CTG TCG CAG ATC TAC GAG
TGG ATG GTC AAG AGC GTG CCC TAC TTC AAG GAT AAG GGT GAC AGC
AAC AGC TCG GCG GGC TGG AAG AAT TCA ATT CGT CAT AAT CTG TCC
CTA CAC AGC AAG TTC ATT CGT GTG CAG AAT GAA GGA ACT GGA AAA
AGT TCT TGG TGG ATG CTC AAT CCA GAG GGT GGC AAG AGC GGG AAA
TCT CCT AGG AGA AGA GCT GCA TCC ATG GAC AAC AAC AGT AAA TTT
GCT AAG AGC CGA AGC CGA GCT GCC

SEQ ID NO: 2  TAT  FoxO-DN  TAT

TAC GGT CGT AAA AAA CGT CGT CAG CGT CGT CGT GCC GCC GCT GGG CCG
CTC GCG GGG CAG CCG CGC AAG AGC AGC TCG TCC CGC CGC AAC GCG TGG
GGC AAC CTG TCC TAC GCC GAC CTC ATC ACC AAG GCC ATC GAG AGC TCG
GCG GAG AAG CGG CTC ACG CTG TCG CAG ATC TAC GAG TGG ATG GTC AAG
AGC GTG CCC TAC TTC AAG GAT AAG GGT GAC AGC AAC AGC TCG GCG GGC
TGG AAG AAT TCA ATT CGT CAT AAT CTG TCC CTA CAC AGC AAG TTC ATT
CGT GTG CAG AAT GAA GGA ACT GGA AAA AGT TCT TGG TGG ATG CTC AAT
CCA GAG GGT GGC AAG AGC GGG AAA TCT CCT AGG AGA AGA GCT GCA TCC
ATG GAC AAC AAC AGT AAA TTT GCT AAG AGC CGA AGC CGA GCT GCC **TAC
GGT CGT AAA AAA CGT CGT CAG CGT CGT CGT**

SEQUENCE LISTING

```
<160> NUMBER OF SEQ ID NOS: 60

<210> SEQ ID NO 1
<211> LENGTH: 429
<212> TYPE: DNA
<213> ORGANISM: Homo sapiens
<220> FEATURE:
<221> NAME/KEY: TAT FoxO-DN
<222> LOCATION: (1)..(429)

<400> SEQUENCE: 1
tacggtcgta aaaaacgtcg tcagcgtcgt cgtgccgccg ctgggccgct cgcggggcag      60
ccgcgcaaga gcagctcgtc ccgccgcaac gcgtggggca acctgtccta cgccgacctc     120
atcaccaagg ccatcgagag ctcggcggag aagcggctca cgctgtcgca gatctacgag     180
tggatggtca agagcgtgcc ctacttcaag gataagggtg acagcaacag ctcggcgggc     240
tggaagaatt caattcgtca taatctgtcc ctacacagca agttcattcg tgtgcagaat     300
gaaggaactg gaaaaagttc ttggtggatg ctcaatccag agggtggcaa gagcgggaaa     360
tctcctagga gaagagctgc atccatggac aacaacagta aatttgctaa gagccgaagc     420
cgagctgcc                                                            429

<210> SEQ ID NO 2
<211> LENGTH: 462
<212> TYPE: DNA
<213> ORGANISM: Homo sapiens
<220> FEATURE:
<221> NAME/KEY: TAT FoxO-DN TAT
<222> LOCATION: (1)..(462)

<400> SEQUENCE: 2
tacggtcgta aaaaacgtcg tcagcgtcgt cgtgccgccg ctgggccgct cgcggggcag      60
ccgcgcaaga gcagctcgtc ccgccgcaac gcgtggggca acctgtccta cgccgacctc     120
atcaccaagg ccatcgagag ctcggcggag aagcggctca cgctgtcgca gatctacgag     180
tggatggtca agagcgtgcc ctacttcaag gataagggtg acagcaacag ctcggcgggc     240
```

```
tggaagaatt caattcgtca taatctgtcc ctacacagca agttcattcg tgtgcagaat    300
gaaggaactg aaaaagttc ttggtggatg ctcaatccag agggtggcaa gagcgggaaa     360
tctcctagga gaagagctgc atccatggac aacaacagta aatttgctaa gagccgaagc    420
cgagctgcct acggtcgtaa aaacgtcgt cagcgtcgtc gt                        462
```

```
<210> SEQ ID NO 3
<211> LENGTH: 21
<212> TYPE: DNA
<213> ORGANISM: Artificial Sequence
<220> FEATURE:
<223> OTHER INFORMATION: Cre-F
<220> FEATURE:
<221> NAME/KEY: primer_bind
<222> LOCATION: (1)..(21)

<400> SEQUENCE: 3
gtccgaccag tttagttacc c                                              21

<210> SEQ ID NO 4
<211> LENGTH: 25
<212> TYPE: DNA
<213> ORGANISM: artificial
<220> FEATURE:
<223> OTHER INFORMATION: Cre-R
<220> FEATURE:
<221> NAME/KEY: primer_bind
<222> LOCATION: (1)..(25)

<400> SEQUENCE: 4
tcgcgattat cttctatatc ttcag                                          25

<210> SEQ ID NO 5
<211> LENGTH: 26
<212> TYPE: DNA
<213> ORGANISM: artificial
<220> FEATURE:
<223> OTHER INFORMATION: oFK1ckA
<220> FEATURE:
<221> NAME/KEY: primer_bind
<222> LOCATION: (1)..(26)

<400> SEQUENCE: 5
gcttagagca gagatgttct cacatt                                         26

<210> SEQ ID NO 6
<211> LENGTH: 26
<212> TYPE: DNA
<213> ORGANISM: artificial
<220> FEATURE:
<223> OTHER INFORMATION: oFK1ckB
<220> FEATURE:
<221> NAME/KEY: primer_bind
<222> LOCATION: (1)..(26)

<400> SEQUENCE: 6
ccagagtctt tgtatcaggc aaataa                                         26

<210> SEQ ID NO 7
<211> LENGTH: 25
<212> TYPE: DNA
<213> ORGANISM: artificial
<220> FEATURE:
<223> OTHER INFORMATION: oFK1ckD
<220> FEATURE:
<221> NAME/KEY: primer_bind
<222> LOCATION: (1)..(25)
```

```
<400> SEQUENCE: 7
caagtccatt aattcagcac attga                                     25

<210> SEQ ID NO 8
<211> LENGTH: 24
<212> TYPE: DNA
<213> ORGANISM: artificial
<220> FEATURE:
<223> OTHER INFORMATION: oFK2ckA
<220> FEATURE:
<221> NAME/KEY: primer_bind
<222> LOCATION: (1)..(24)

<400> SEQUENCE: 8
attcctttgg aaatcaacaa aact                                      24

<210> SEQ ID NO 9
<211> LENGTH: 25
<212> TYPE: DNA
<213> ORGANISM: artificial
<220> FEATURE:
<223> OTHER INFORMATION: oFK2ckB
<220> FEATURE:
<221> NAME/KEY: primer_bind
<222> LOCATION: (1)..(25)

<400> SEQUENCE: 9
tgctttgata ctattccaca aaccc                                     25

<210> SEQ ID NO 10
<211> LENGTH: 25
<212> TYPE: DNA
<213> ORGANISM: artificial
<220> FEATURE:
<223> OTHER INFORMATION: oFK2ckD
<220> FEATURE:
<221> NAME/KEY: primer_bind
<222> LOCATION: (1)..(25)

<400> SEQUENCE: 10
agatttatgt tcccacttgc ttcct                                     25

<210> SEQ ID NO 11
<211> LENGTH: 25
<212> TYPE: DNA
<213> ORGANISM: artificial
<220> FEATURE:
<223> OTHER INFORMATION: oAFXckD
<220> FEATURE:
<221> NAME/KEY: primer_bind
<222> LOCATION: (1)..(25)

<400> SEQUENCE: 11
cttctctgtg ggaataaatg tttgg                                     25

<210> SEQ ID NO 12
<211> LENGTH: 24
<212> TYPE: DNA
<213> ORGANISM: artificial
<220> FEATURE:
<223> OTHER INFORMATION: oAFXckE
<220> FEATURE:
<221> NAME/KEY: primer_bind
<222> LOCATION: (1)..(24)

<400> SEQUENCE: 12
ctacttcaag gacaagggtg acag                                      24
```

```
<210> SEQ ID NO 13
<211> LENGTH: 22
<212> TYPE: DNA
<213> ORGANISM: artificial
<220> FEATURE:
<223> OTHER INFORMATION: oAFXckM
<220> FEATURE:
<221> NAME/KEY: primer_bind
<222> LOCATION: (1)..(22)

<400> SEQUENCE: 13
tgagaagcca ttgaagatca ga                                              22

<210> SEQ ID NO 14
<211> LENGTH: 20
<212> TYPE: DNA
<213> ORGANISM: artificial
<220> FEATURE:
<223> OTHER INFORMATION: myogenin-F
<220> FEATURE:
<221> NAME/KEY: primer_bind
<222> LOCATION: (1)..(20)

<400> SEQUENCE: 14
atctccgcta cagaggcggg                                                 20

<210> SEQ ID NO 15
<211> LENGTH: 20
<212> TYPE: DNA
<213> ORGANISM: artificial
<220> FEATURE:
<223> OTHER INFORMATION: myogenin-R
<220> FEATURE:
<221> NAME/KEY: primer_bind
<222> LOCATION: (1)..(20)

<400> SEQUENCE: 15
tagggtcagc cgcgagcaaa                                                 20

<210> SEQ ID NO 16
<211> LENGTH: 20
<212> TYPE: DNA
<213> ORGANISM: artificial
<220> FEATURE:
<223> OTHER INFORMATION: HDAC4-F
<220> FEATURE:
<221> NAME/KEY: primer_bind
<222> LOCATION: (1)..(20)

<400> SEQUENCE: 16
agagagtgct gtggcgagca                                                 20

<210> SEQ ID NO 17
<211> LENGTH: 20
<212> TYPE: DNA
<213> ORGANISM: artificial
<220> FEATURE:
<223> OTHER INFORMATION: HDAC4-R
<220> FEATURE:
<221> NAME/KEY: primer_bind
<222> LOCATION: (1)..(20)

<400> SEQUENCE: 17
acggggtggt tgtaggaggc                                                 20

<210> SEQ ID NO 18
<211> LENGTH: 22
<212> TYPE: DNA
```

```
<213> ORGANISM: artificial
<220> FEATURE:
<223> OTHER INFORMATION: Atrogin-F
<220> FEATURE:
<221> NAME/KEY: primer_bind
<222> LOCATION: (1)..(22)

<400> SEQUENCE: 18
caacattaac atgtgggtgt at                                              22

<210> SEQ ID NO 19
<211> LENGTH: 19
<212> TYPE: DNA
<213> ORGANISM: artificial
<220> FEATURE:
<223> OTHER INFORMATION: Atrogin-R
<220> FEATURE:
<221> NAME/KEY: primer_bind
<222> LOCATION: (1)..(19)

<400> SEQUENCE: 19
gtcactcagc ctctgcatg                                                  19

<210> SEQ ID NO 20
<211> LENGTH: 20
<212> TYPE: DNA
<213> ORGANISM: artificial
<220> FEATURE:
<223> OTHER INFORMATION: MuRF1-F
<220> FEATURE:
<221> NAME/KEY: primer_bind
<222> LOCATION: (1)..(20)

<400> SEQUENCE: 20
gagaacctgg agaagcagct                                                 20

<210> SEQ ID NO 21
<211> LENGTH: 18
<212> TYPE: DNA
<213> ORGANISM: artificial
<220> FEATURE:
<223> OTHER INFORMATION: MuRF1-R
<220> FEATURE:
<221> NAME/KEY: primer_bind
<222> LOCATION: (1)..(18)

<400> SEQUENCE: 21
ccgcggttgg tccagtag                                                   18

<210> SEQ ID NO 22
<211> LENGTH: 26
<212> TYPE: DNA
<213> ORGANISM: artificial
<220> FEATURE:
<223> OTHER INFORMATION: actin-gamma R
<220> FEATURE:
<221> NAME/KEY: primer_bind
<222> LOCATION: (1)..(26)

<400> SEQUENCE: 22
ccatctagaa gcatttgcgg tggacg                                          26

<210> SEQ ID NO 23
<211> LENGTH: 24
<212> TYPE: DNA
<213> ORGANISM: artificial
<220> FEATURE:
<223> OTHER INFORMATION: actin-gamma F
<220> FEATURE:
```

```
<221> NAME/KEY: primer_bind
<222> LOCATION: (1)..(24)

<400> SEQUENCE: 23
acccaggcat tgctgacagg atgc                                              24

<210> SEQ ID NO 24
<211> LENGTH: 20
<212> TYPE: DNA
<213> ORGANISM: artificial
<220> FEATURE:
<223> OTHER INFORMATION: TSC1-F
<220> FEATURE:
<221> NAME/KEY: primer_bind
<222> LOCATION: (1)..(20)

<400> SEQUENCE: 24
gtcaatgagc tgtacctgga                                                   20

<210> SEQ ID NO 25
<211> LENGTH: 20
<212> TYPE: DNA
<213> ORGANISM: artificial
<220> FEATURE:
<223> OTHER INFORMATION: TSC1-R
<220> FEATURE:
<221> NAME/KEY: primer_bind
<222> LOCATION: (1)..(20)

<400> SEQUENCE: 25
ctttggttct gctggagaag                                                   20

<210> SEQ ID NO 26
<211> LENGTH: 18
<212> TYPE: DNA
<213> ORGANISM: artificial
<220> FEATURE:
<223> OTHER INFORMATION: FoxO1-F
<220> FEATURE:
<221> NAME/KEY: primer_bind
<222> LOCATION: (1)..(18)

<400> SEQUENCE: 26
cgcgcaagac cagctcgt                                                     18

<210> SEQ ID NO 27
<211> LENGTH: 20
<212> TYPE: DNA
<213> ORGANISM: artificial
<220> FEATURE:
<223> OTHER INFORMATION: Fox-O1-R
<220> FEATURE:
<221> NAME/KEY: primer_bind
<222> LOCATION: (1)..(20)

<400> SEQUENCE: 27
tccgctcttg cctccctctg                                                   20

<210> SEQ ID NO 28
<211> LENGTH: 22
<212> TYPE: DNA
<213> ORGANISM: artificial
<220> FEATURE:
<223> OTHER INFORMATION: FoxO3-F
<220> FEATURE:
<221> NAME/KEY: primer_bind
<222> LOCATION: (1)..(22)

<400> SEQUENCE: 28
```
ggataagggc gacagcaaca gc                                              22

<210> SEQ ID NO 29
<211> LENGTH: 22
<212> TYPE: DNA
<213> ORGANISM: artificial
<220> FEATURE:
<223> OTHER INFORMATION: FoxO3-R

<400> SEQUENCE: 29
gcctcggctc ttggtgtact tg                                              22

<210> SEQ ID NO 30
<211> LENGTH: 20
<212> TYPE: DNA
<213> ORGANISM: artificial
<220> FEATURE:
<223> OTHER INFORMATION: FoxO4-F
<220> FEATURE:
<221> NAME/KEY: primer_bind
<222> LOCATION: (1)..(20)

<400> SEQUENCE: 30
ggagaagcgg ctgacactcg                                                 20

<210> SEQ ID NO 31
<211> LENGTH: 20
<212> TYPE: DNA
<213> ORGANISM: artificial
<220> FEATURE:
<223> OTHER INFORMATION: FoxO4-R
<220> FEATURE:
<221> NAME/KEY: primer_bind
<222> LOCATION: (1)..(20)

<400> SEQUENCE: 31
cttgccagtg gcctcgttgt                                                 20

<210> SEQ ID NO 32
<211> LENGTH: 21
<212> TYPE: DNA
<213> ORGANISM: Artificial Sequence
<220> FEATURE:
<223> OTHER INFORMATION: Cre-F

<400> SEQUENCE: 32
gctcgaccag tttagttacc c                                               21

<210> SEQ ID NO 33
<211> LENGTH: 22
<212> TYPE: DNA
<213> ORGANISM: Artificial Sequence
<220> FEATURE:
<223> OTHER INFORMATION: Cre-R

<400> SEQUENCE: 33
tcgcgattat ctatatcttc ag                                              22

<210> SEQ ID NO 34
<211> LENGTH: 26
<212> TYPE: DNA
<213> ORGANISM: Artificial Sequence
<220> FEATURE:
<223> OTHER INFORMATION: oFK1ckA

<400> SEQUENCE: 34
gcttagagca gagatgttct cacatt                                          26

<210> SEQ ID NO 35
<211> LENGTH: 26
<212> TYPE: DNA
<213> ORGANISM: Artificial Sequence
<220> FEATURE:
<223> OTHER INFORMATION: oFK1ckB

<400> SEQUENCE: 35
ccagagtctt tgtatcaggc aaataa                                          26

<210> SEQ ID NO 36
<211> LENGTH: 25
<212> TYPE: DNA
<213> ORGANISM: Artificial Sequence
<220> FEATURE:
<223> OTHER INFORMATION: oFK1ckD

<400> SEQUENCE: 36
caagtccatt aattcagcac attga                                           25

<210> SEQ ID NO 37
<211> LENGTH: 24
<212> TYPE: DNA
<213> ORGANISM: Artificial Sequence
<220> FEATURE:
<223> OTHER INFORMATION: oFK2ckA

<400> SEQUENCE: 37
attcctttgg aaatcaacaa aact                                            24

<210> SEQ ID NO 38
<211> LENGTH: 25
<212> TYPE: DNA
<213> ORGANISM: Artificial Sequence
<220> FEATURE:
<223> OTHER INFORMATION: oFK2ckB

<400> SEQUENCE: 38
tgctttgata ctattccaca aaccc                                           25

<210> SEQ ID NO 39
<211> LENGTH: 25
<212> TYPE: DNA
<213> ORGANISM: Artificial Sequence
<220> FEATURE:
<223> OTHER INFORMATION: oFK2ckD

<400> SEQUENCE: 39
agatttatgt tcccacttgc ttcct                                           25

<210> SEQ ID NO 40
<211> LENGTH: 25
<212> TYPE: DNA
<213> ORGANISM: Artificial Sequence
<220> FEATURE:
<223> OTHER INFORMATION: oAFXckD

<400> SEQUENCE: 40
cttctctgtg ggaataaatg tttgg                                           25

<210> SEQ ID NO 41
<211> LENGTH: 24
<212> TYPE: DNA
<213> ORGANISM: Artificial Sequence

```
<220> FEATURE:
<223> OTHER INFORMATION: oAFXckE

<400> SEQUENCE: 41
ctacttcaag gacaagggtg acag                                          24

<210> SEQ ID NO 42
<211> LENGTH: 22
<212> TYPE: DNA
<213> ORGANISM: Artificial Sequence
<220> FEATURE:
<223> OTHER INFORMATION: oAFXckM

<400> SEQUENCE: 42
tgagaagcca ttgaagatca ga                                            22

<210> SEQ ID NO 43
<211> LENGTH: 20
<212> TYPE: DNA
<213> ORGANISM: Artificial Sequence
<220> FEATURE:
<223> OTHER INFORMATION: myogenin-F

<400> SEQUENCE: 43
atctccgcta cagaggcggg                                               20

<210> SEQ ID NO 44
<211> LENGTH: 20
<212> TYPE: DNA
<213> ORGANISM: Artificial Sequence
<220> FEATURE:
<223> OTHER INFORMATION: myogenin-R

<400> SEQUENCE: 44
tagggtcagc cgcgagcaaa                                               20

<210> SEQ ID NO 45
<211> LENGTH: 20
<212> TYPE: DNA
<213> ORGANISM: Artificial Sequence
<220> FEATURE:
<223> OTHER INFORMATION: HDAC4-F

<400> SEQUENCE: 45
agagagtgct gtggcgagca                                               20

<210> SEQ ID NO 46
<211> LENGTH: 20
<212> TYPE: DNA
<213> ORGANISM: Artificial Sequence
<220> FEATURE:
<223> OTHER INFORMATION: HDAC4-R

<400> SEQUENCE: 46
acggggtggt tgtaggaggc                                               20

<210> SEQ ID NO 47
<211> LENGTH: 22
<212> TYPE: DNA
<213> ORGANISM: Artificial Sequence
<220> FEATURE:
<223> OTHER INFORMATION: Atrogin-F

<400> SEQUENCE: 47
caacattaac atgtgggtgt at                                            22
```

<210> SEQ ID NO 48
<211> LENGTH: 19
<212> TYPE: DNA
<213> ORGANISM: Artificial Sequence
<220> FEATURE:
<223> OTHER INFORMATION: Atrogin-R

<400> SEQUENCE: 48
gtcactcagc ctctgcatg                                              19

<210> SEQ ID NO 49
<211> LENGTH: 20
<212> TYPE: DNA
<213> ORGANISM: Artificial Sequence
<220> FEATURE:
<223> OTHER INFORMATION: MuRF1-F

<400> SEQUENCE: 49
gagaacctgg agaagcagct                                             20

<210> SEQ ID NO 50
<211> LENGTH: 18
<212> TYPE: DNA
<213> ORGANISM: Artificial Sequence
<220> FEATURE:
<223> OTHER INFORMATION: MuRF1-R

<400> SEQUENCE: 50
ccgcggttgg tccagtag                                               18

<210> SEQ ID NO 51
<211> LENGTH: 26
<212> TYPE: DNA
<213> ORGANISM: Artificial Sequence
<220> FEATURE:
<223> OTHER INFORMATION: actin-gamma R

<400> SEQUENCE: 51
ccatctagaa gcatttgcgg tggacg                                      26

<210> SEQ ID NO 52
<211> LENGTH: 24
<212> TYPE: DNA
<213> ORGANISM: Artificial Sequence
<220> FEATURE:
<223> OTHER INFORMATION: actin-gamma F

<400> SEQUENCE: 52
acccaggcat tgctgacagg atgc                                        24

<210> SEQ ID NO 53
<211> LENGTH: 20
<212> TYPE: DNA
<213> ORGANISM: Artificial Sequence
<220> FEATURE:
<223> OTHER INFORMATION: TSC1-F

<400> SEQUENCE: 53
gtcaatgagc tgtacctgga                                             20

<210> SEQ ID NO 54
<211> LENGTH: 20
<212> TYPE: DNA
<213> ORGANISM: Artificial Sequence
<220> FEATURE:
<223> OTHER INFORMATION: TSC1-R

```
<400> SEQUENCE: 54
ctttggttct gctggagaag                                                   20

<210> SEQ ID NO 55
<211> LENGTH: 18
<212> TYPE: DNA
<213> ORGANISM: Artificial Sequence
<220> FEATURE:
<223> OTHER INFORMATION: FoxO1-F

<400> SEQUENCE: 55
cgcgcaagac cagctcgt                                                     18

<210> SEQ ID NO 56
<211> LENGTH: 20
<212> TYPE: DNA
<213> ORGANISM: Artificial Sequence
<220> FEATURE:
<223> OTHER INFORMATION: FoxO1-R

<400> SEQUENCE: 56
tccgctcttg cctccctctg                                                   20

<210> SEQ ID NO 57
<211> LENGTH: 22
<212> TYPE: DNA
<213> ORGANISM: Artificial Sequence
<220> FEATURE:
<223> OTHER INFORMATION: FoxO3-F

<400> SEQUENCE: 57
ggataagggc gacagcaaca gc                                                22

<210> SEQ ID NO 58
<211> LENGTH: 22
<212> TYPE: DNA
<213> ORGANISM: Artificial Sequence
<220> FEATURE:
<223> OTHER INFORMATION: FoxO3-R

<400> SEQUENCE: 58
gcctcggctc ttggtgtact tg                                                22

<210> SEQ ID NO 59
<211> LENGTH: 20
<212> TYPE: DNA
<213> ORGANISM: Artificial Sequence
<220> FEATURE:
<223> OTHER INFORMATION: FoxO4-F

<400> SEQUENCE: 59
ggagaagcgg ctgacactcg                                                   20

<210> SEQ ID NO 60
<211> LENGTH: 20
<212> TYPE: DNA
<213> ORGANISM: Artificial Sequence
<220> FEATURE:
<223> OTHER INFORMATION: FoxO4-R

<400> SEQUENCE: 60
cttgccagtg gcctcgttgt                                                   20
```

METHODS FOR TREATING DENERVATION-INDUCED MUSCLE ATROPHY

RELATED APPLICATION

This application claims priority and other benefits from U.S. Provisional Patent Application Ser. No. 61/791,249, filed Mar. 15, 2013, entitled "Methods for treating muscle atrophy". Its entire content is specifically incorporated herein by reference.

INCORPORATION OF SEQUENCE LISTING

A computer readable form of the sequence listing, "S12_197_substitute_sequences_ST25.txt," submitted via EFS-WEB, is herein incorporated by reference.

TECHNICAL FIELD OF THE INVENTION

The invention relates generally to the treatment of skeletal muscle pathologies, and more particularly, to the administration of agents which decrease the activity of the mammalian target of rapamycin and/or the activity of at least one of Forkhead Box Transcription Factors 1, 3 and 4 for the treatment of denervation-induced skeletal muscle degeneration diseases and related muscle wasting disorders.

BACKGROUND

The maintenance of skeletal muscle mass is controlled by a balance between protein synthesis and protein degradation which the muscle fibers dynamically regulate in order to adapt to differential levels of physical activity. When the balance favors protein synthesis, muscle mass increases, when the balance favors proteolysis, muscle mass decreases and the muscle atrophies. Factors that lead to muscle atrophy include muscle injury, joint immobilization, prolonged bed rest, glucocorticoid treatment, sepsis, cancer, aging and muscle denervation.

ATP-dependent protein degradation, mediated by the ubiquitin proteasome system (UPS), is increased in atrophying muscle through activation of the muscle-specific E3 ubiquitin ligases atrogin (also known as MAFbx, muscle atrophy F box protein) and MuRF1 (muscle-specific ring finger 1) (Bodine et al., 2001a; Gomes et al., 2001; Lecker et al., 2004). Use of a proteasome inhibitor (Beehler et al., 2006) or genetic deletion of each of the E3 ubiquitin ligases, reduces denervation muscle atrophy (Bodine et al., 2001a), indicating that UPS-mediated protein degradation is a major pathway underlying this process.

Muscle innervation is an important regulator of skeletal muscle mass and function. Individuals, who as a consequence of traumatic nerve injury and motor neuron diseases experience a loss of motor innervation, suffer from highly morbid denervation-associated muscle atrophy for which there is currently no effective therapy. Blocking or reversing denervation-associated muscle atrophy would be an important step towards reducing the extent of permanent damage that results from motor neuron injuries.

SUMMARY OF THE INVENTION

One aspect of the present invention is to provide methods of attenuating skeletal muscle atrophy in a mammalian subject, comprising administering to said subject suffering from denervation-induced skeletal muscle atrophy a composition comprising an agent that decreases activity of mammalian target of rapamycin in a dosage and dosing regimen effective to attenuate denervation-induced skeletal muscle atrophy.

A further aspect of the present invention is to provide methods of preventing skeletal muscle atrophy in a mammalian subject, comprising administering to said subject being at risk of developing a denervation-induced skeletal muscle atrophy a composition comprising an agent that decreases activity of mammalian target of rapamycin in a dosage and dosing regimen effective to prevent denervation-induced skeletal muscle atrophy.

Another aspect of the present invention is to provide methods of attenuating skeletal muscle atrophy in a mammalian subject, comprising administering to said subject suffering from denervation-induced skeletal muscle atrophy a composition comprising an agent that decreases activity of at least one of Forkhead Box Transcription Factors 1, 3 and 4 in a dosage and dosing regimen effective to attenuate denervation-induced skeletal muscle atrophy.

Yet another aspect of the present invention is to provide methods of preventing skeletal muscle atrophy in a mammalian subject, comprising administering to said subject being at risk of developing a denervation-induced skeletal muscle atrophy a composition comprising an agent that decreases activity of at least one of Forkhead Box Transcription Factors 1, 3 and 4 in a dosage and dosing regimen effective to prevent skeletal muscle atrophy.

A further aspect of the present invention is to provide methods of attenuating skeletal muscle atrophy in a mammalian subject, comprising administering to said subject suffering from a denervation-induced skeletal muscle atrophy a composition comprising an agent that decreases the activity of mammalian target of rapamycin as well as a composition comprising an agent that decreases activity of at least one of Forkhead Box Transcription Factors 1, 3 and 4, whereby the administering of the agents is performed sequentially, either one being administered first or second, or simultaneously.

Another aspect of the present invention is to provide methods of preventing skeletal muscle atrophy in a mammalian subject, comprising administering to said subject suffering from a denervation-induced skeletal muscle atrophy a composition comprising an agent that decreases the activity of mammalian target of rapamycin as well as a composition comprising an agent that decreases activity of at least one of Forkhead Box Transcription Factors 1, 3 and 4, whereby the administering of the agents is performed sequentially, either one being administered first or second, or simultaneously.

In the various embodiments of the present invention, the muscle atrophy results from a traumatic nerve injury, a neurodegenerative motor neuron disease, sarcopenia or from muscle disuse.

In certain embodiments of the present invention the agent that decreases the activity of the mammalian target of rapamycin is an inhibitor of the mTOR complex 1. In other embodiments of the present invention the agent that decreases the activity of the mammalian target of rapamycinis a dual inhibitor of the mTOR complex 1 and mTOR complex 2.

In certain embodiments of the present invention the agent that decreases the activity of at least one of Forkhead Box Transcription Factors 1, 3 and 4 has SEQ NO 1 or 2.

In certain embodiments of the present invention the agent that decreases the activity of at least one of Forkhead Box Transcription Factors 1, 3 and 4 has a sequence that is identical or substantially identical to Sequence ID No. 1 or 2 (see FIG. 6).

INCORPORATION BY REFERENCE

All publications mentioned in this specification are herein incorporated by reference to the same extent as if each individual publication was specifically and individually indicated to be incorporated by reference.

BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

FIG. 4 illustrates that inhibition of mTORC1 activity by rapamycin mitigates denervation muscle atrophy via regulating FoxO. Inhibition of mTORC1 activity with rapamycin treatment partially rescues fiber size (A) and weight (B) in muscle 15 days after denervation. A) Cross sectional area (CSA) of muscle fibers stained with WGA. The innervated, contralateral control was set at 100% and indicated by the horizontal, dotted line. At least 600 fibers/muscle utilized, n=6 mice, *p<0.05. Representative images were shown, scale bar, 50 μm. B) Denervated muscle weight (TA and gastrocnemius) was normalized to the contralateral innervated muscles, which was set at 100% and indicated by the horizontal, dotted line (n=6 mice per genotype and treatment, *p<0.05). C) mRNA expression of atrogin and MuRF1 was normalized to γ-actin. Fold changes was calculated as the ratio of mRNA in denervated muscles to that in their contralateral controls (n=6 mice per genotype and treatment, *p<0.05). D) Total protein extracts from gastrocnemius muscles were immunoblotted with antibodies against ubiquitin and actin. Actin was used as the loading control. n=2 mice per genotype and treatment. E) Myogenin mRNA abundance was measured. n=6 mice per genotype and treatment, *p<0.05. F) Western blot analysis was performed on protein extracts from gastrocnemius muscles to measure the phosphorylation and total abundance of the indicated proteins. Equal loading was shown by Ponceau S staining and actin. Phosphorylation of a protein was normalized to the total abundance protein and fold changes were shown (right). n=2 mice per genotype and treatment. G) FoxO is required for the protective effect of rapamcyin. Control or FoxO-DN constructs and a GFP-expressing reporter gene were electroporated into denervated TA muscles. Rapamycin was administered and 15 days after denervation, the CSAs of the GFP+ fibers (>80) in TA muscles were measured and normalized to the contralateral innervated control. Representative images were shown, scale bar, 50 μm. n=3 mice per genotype and treatment, *p<0.05, ns, no significant difference. H) A dominant negative FoxO (FoxO-DN) construct, containing the DNA binding domain and nuclear localization signal, was established to block FoxO activity. I) FoxO-DN blocks FoxO-induced reporter gene activity. The FoxO reporter gene 6DBE was cotransfected with FoxO1, in the presence and absence of FoxO-DN, into C2C12 cells, and luciferase activity was measured (n=3 independent experiments, *p<0.05). J) FoxO-DN inhibits atrogin promoter activity. Atrogin promoter reporter gene was transfected into C2C12 cells, with and without FoxO-DN construct (n=3 independent experiments, *p<0.05).

FIG. 6 shows a human dominant negative FoxO-TAT fusion protein with a 10-amino acid peptide TAT tag at the N-terminus (SEQ ID NO:1) and a human dominant negative FoxO-TAT fusion protein with a TAT tag at both the N-terminus and the C-terminus (SEQ ID NO:2). The TAT tag sequences are shown in bold. These FoxO fusion proteins are capable of penetrating cell membranes and decreasing the activity of Fox1, 3 and 4. The human dominant negative FoxO-TAT fusion proteins lack the transactivation domains of FoxO1 but have retained the DNA binding domain and a nuclear translocation signal.

DETAILED DESCRIPTION

Figure 1:
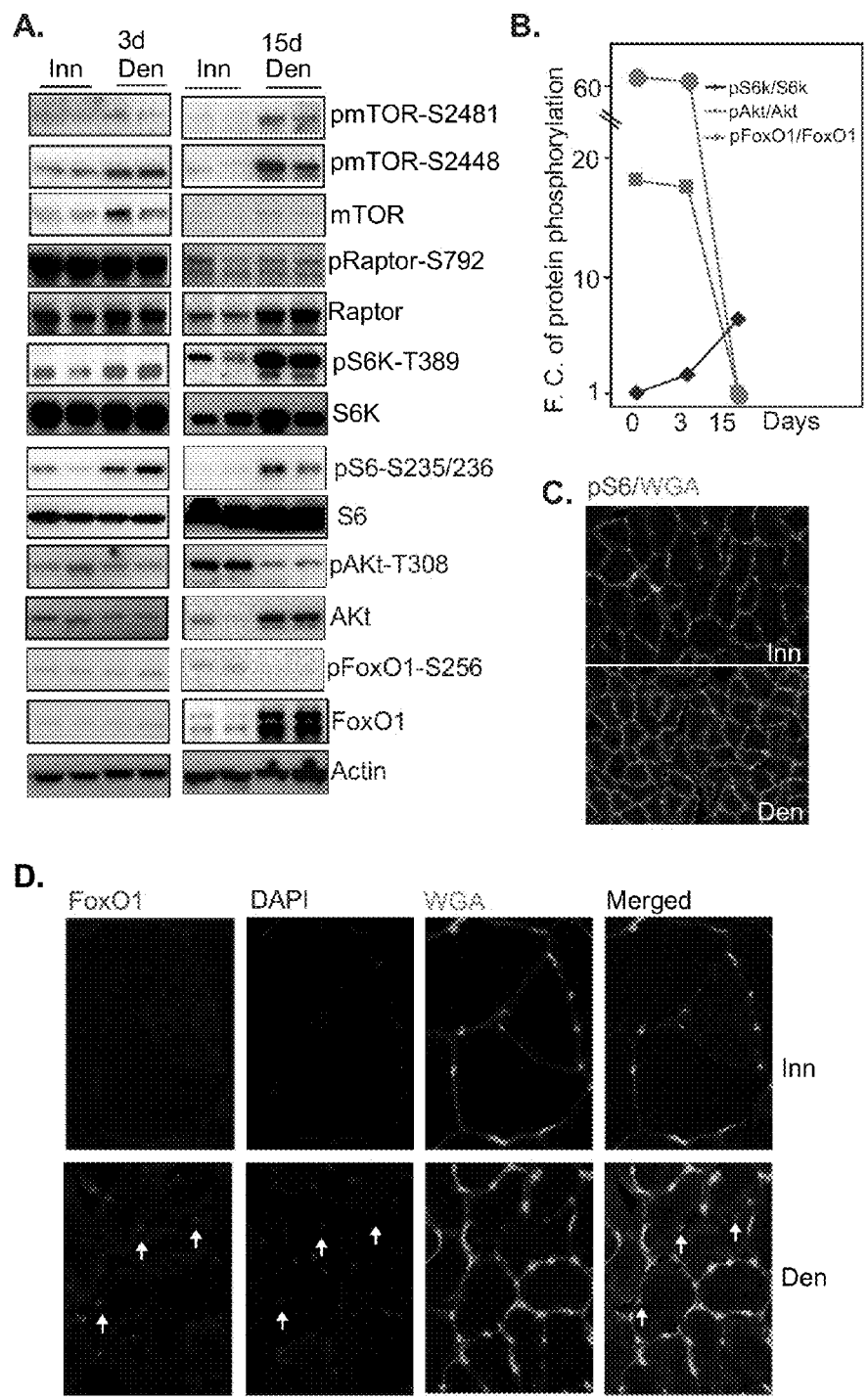
FIG. 1 illustrates the time-dependent regulation of mTORC1-S6K and Akt-FoxO pathways in response to skeletal muscle denervation. A) Protein extracts from gastrocnemius muscles 3 and 15 days after denervation were subjected to Western blot analysis. Actin was used as loading control. Inn: innervated; Den: denervated. (n=2 randomly selected mice per treatment shown; see materials and methods). B) The temporal pattern of the phosphorylation of S6K, Akt and FoxO1 after muscle denervation. The phosphorylated and total proteins were quantified and fold change (FC) is shown as denervated compared to innervated (n=2 randomly selected mice per treatment). C) Confocal images of cryosections of innervated and denervated (15 days) tibialis anterior (TA) muscles that were co-stained with anti-pS6 (red) and the membrane marker wheat germ agglutinin (WGA, green). Scale bar, 50 μm. Images are representative of 3 mice per treatment. D) Confocal images of cryosections of innervated and denervated (15 days) TA muscle stained with anti-FoxO1 (red), WGA (green) and DAPI (blue). Scale bar, 15 μm. Images are representative of 3 mice per treatment.

The invention described below relates to (i) methods for attenuating skeletal muscle atrophy in a mammalian subject suffering from denervation-induced skeletal muscle atrophy and to (ii) methods for preventing skeletal muscle atrophy in a mammalian subject being at risk of developing a denervation-induced skeletal muscle atrophy, by decreasing the activity of mammalian target of rapamycin or the activity of at least one of the Forkhead Box Transcription Factors 1, 3 and 4 or by decreasing the activity of both.

Before describing detailed embodiments of the invention, it will be useful to set forth definitions that are utilized in describing the present invention.

DEFINITIONS

The practice of the present invention may employ conventional techniques of chemistry, molecular biology, recombinant DNA, microbiology, cell biology, immunology and biochemistry, which are within the capabilities of a person of ordinary skill in the art. Such techniques are fully explained in the literature. For definitions, terms of art and standard methods known in the art, see, for example, Sambrook and Russell 'Molecular Cloning: A Laboratory Manual', Cold Spring Harbor Laboratory Press (2001); 'Current Protocols in Molecular Biology', John Wiley & Sons (2007); William Paul 'Fundamental Immunology', Lippincott Williams & Wilkins (1999); M. J. Gait 'Oligonucleotide Synthesis: A Practical Approach', Oxford University Press (1984); R. Ian Freshney "Culture of Animal Cells: A Manual of Basic Technique", Wiley-Liss (2000); 'Current Protocols in Microbiology', John Wiley & Sons (2007); 'Current Protocols in Cell Biology', John Wiley & Sons (2007); Wilson & Walker 'Principles and Techniques of Practical Biochemistry', Cambridge University Press (2000); Roe, Crabtree, & Kahn 'DNA Isolation and Sequencing: Essential Techniques', John Wiley & Sons (1996); D. Lilley & Dahlberg 'Methods of Enzymology: DNA Structure Part A: Synthesis and Physical Analysis of DNA Methods in Enzymology', Academic Press (1992); Harlow & Lane 'Using Antibodies: A Laboratory Manual: Portable Protocol No. I', Cold Spring Harbor Laboratory Press (1999); Harlow & Lane 'Antibodies: A Laboratory Manual', Cold Spring Harbor Laboratory Press (1988); Roskams & Rodgers 'Lab Ref: A Handbook of Recipes, Reagents, and Other Reference Tools for Use at the Bench', Cold Spring Harbor Laboratory Press (2002). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise.

The term "attenuate" or "attenuating" is used interchangeably with "treat" or "treating", "decrease" or "decreasing" and, as used herein, refers to accomplishing one or more of the following: reducing the severity of a disorder, limiting or eliminating the symptoms characteristic of the disorder being treated, limiting or reversing the worsening of symptoms characteristic of the disorder being treated.

The terms "degeneration" and "degenerated" are herein used equivalent to the terms "atrophy" and "atrophic".

The term "denervation-induced skeletal muscle atrophy" or "denervation-induced muscle atrophy" or "denervation-induced atrophy", as used herein, refers to the loss of muscle tissue and/or loss of muscle function resulting either from a neurodegenerative motoneuron disease (neurogenic atrophy), traumatic nerve injury (traumatic atrophy), sarcopenia or lack of use (disuse atrophy).

The term "activity" or "biological activity", as used herein, refers to the biological function or effector function that is directly or indirectly performed by particular proteins such as Forkhead Box Transcription Factors 1, 3, 4 or the mammalian target of rapamycin.

Agents that decrease the activity of the mammalian target of rapamycin (mTOR) or of any of the Forkhead Box Transcription Factors 1, 3 and 4 are also referred herein as 'inhibitors' of the mammalian target of rapamycin or 'inhibitors' of the Forkhead Box Transcription Factors 1, 3 and/or 4.

The term "pharmaceutical composition", as used herein, refers to a mixture of an inhibitor of mTOR or an inhibitor of FoxO1, 3 and/or 4 with chemical components such as diluents or carriers that do not cause unacceptable, i.e. counterproductive to the desired therapeutic effect, adverse side effects and that do not prevent the inhibitor of mTOR or the inhibitor of FoxO1, 3 and/or 4 from exerting a therapeutic effect. A pharmaceutical composition serves to facilitate the administration of the inhibitors.

The term "therapeutic effect", as used herein, refers to a consequence of treatment that might intend either to bring remedy to an injury that already occurred or to prevent an injury before it occurs. A therapeutic effect may include, directly or indirectly, the attenuation, decrease and mitigation of skeletal muscle atrophy, degeneration and loss. A therapeutic effect may also include, directly or indirectly, the arrest, reduction, or elimination of the progression of skeletal muscle atrophy, degeneration and loss. A therapeutic effect may, furthermore, also include an in improvement of skeletal muscle function.

The terms "therapeutically effective amount" and "dosage and dosing regimen effective to attenuate muscle atrophy" relate to an amount of an mTOR inhibitor or inhibitor of FoxO1, 3 and/or 4 that is sufficient to provide a desired therapeutic effect in a mammalian subject. Naturally, dosage levels of the particular mTOR inhibitor or inhibitor of FoxO1, 3 and/or 4 employed to provide a therapeutically effective amount vary in dependence of the type of injury, the age, the weight, the gender, the medical condition of the human subject, the severity of the condition, the route of administration, and the particular inhibitor employed. Therapeutically effective amounts of mTOR inhibitors or inhibitors of FoxO1, 3 and/or 4, as described herein, can be estimated initially from cell culture and animal models. For example, $IC_{50}$ values determined in cell culture methods can serve as a starting point in animal models, while $IC_{50}$ values determined in animal models can be used to find a therapeutically effective dose in humans.

The term "dosing regimen", as used herein, refers to the administration schedule and administration intervals of mTOR inhibitors or inhibitors of FoxO1, 3 and/or 4 employed to obtain the desired therapeutic effect.

The term "sequence identity" in the context of two amino acid sequences refers to the residues in the two sequences, which are the same when aligned for maximum correspondence. Optimal alignment of sequences for comparison can be conducted, e.g., by the local homology algorithm of Smith & Waterman, 1981; by the homology alignment algorithm of Needleman & Wunsch, 1970; by the search for similarity method of Pearson & Lipman, 1988; by computerized implementations of these algorithms (GAP, BESTFIT, FASTA, and TFASTA in the Wisconsin Genetics Software Package, Genetics Computer Group, 575 Science Dr., Madison, Wis.), or by inspection. Sequence identity may be calculated on the basis of residues identical to a reference sequence. For example, for a peptide with 8 residues, one may create a peptide variant with 5 identical residues, resulting in a 5/8 or 63% sequence identity. One may also have 6/8 (75%) or 7/8 (88%) sequence identity.

The terms "substantial sequence identity" or "substantial identity" or "substantially identical", as used herein, denote a characteristic of an amino acid or nucleic acid sequence, wherein the peptide, protein or nucleotide comprises a sequence that has at least 60 percent sequence identity, at least 65 percent sequence identity, at least 70 percent sequence identity, at least 75 percent sequence identity, at least 80 percent sequence identity, preferably at least 85 percent identity and often 90 to 95 percent sequence identity, more usually at least 99 percent sequence identity as compared to a reference sequence over a comparison window of the entire length of the peptide, protein or nucleotide.

Neuromuscular Activity and Innervation

Every mammal carries three different muscle types consisting of the cardiac muscle, smooth muscles and skeletal muscles. Only the latter are capable of voluntary movements. A voluntary contraction of a skeletal muscle requires the recruitment of motor neurons which propagate signals ('fire') for contraction over large distances. Each motor neuron innervates a number of muscle fibers that fire one-on-one with the motor neuron and together with the motor neuron comprise a motor unit. When a motor unit fires, the muscle fibers produce a voluntary contraction.

The protein composition, mass and size of a skeletal muscle are generally a function of its neuromuscular activity, i.e. activation and loading, and a function of its nutrition status. The muscle tissue is an important reservoir of proteins within the body and consequently subject to high protein turnover rates, which affords the body to exert control over cell growth and metabolism and allows adaption to physiological changes quickly. Protein breakdown is a causative factor in muscle wasting.

Under the control of the somatic nervous system, due to innervation by somatic motor neurons or motoneurons, messages from nerve cells in the central nervous system, which are the upper motor neurons, are transmitted to nerve cells in the brain stem and spinal cord, which are the lower motor neurons, and from there to the various skeletal muscles enabling voluntary movements. Upper motor neurons control voluntary movements such as walking and chewing, while lower motor neurons control voluntary movements of the arms, legs, chest, face, throat and tongue.

Muscle Atrophy: Loss of Muscle Function and Muscle Mass Due to Denervation

When the information transfer between the nerve cells and the skeletal muscles is impaired or even disrupted, as it happens with traumatic nerve injuries and inherited motor neuron diseases that gradually lead to denervation, the muscles can no longer function properly and begin to become atrophic.

Denervation is an injury to the peripheral motoneurons with a partial or completion interruption of the nerve fibers between an organ and the central nervous system, resulting in an interruption of nerve conduction and motoneuron firing which, in turn, prevents the contractability of skeletal muscles. This loss of nerve function can be localized or generalized due to the loss of an entire motor neuron unit. The resulting inability of skeletal muscles to contract leads to muscle atrophy; within only a few week weeks, a major part of the muscle muss can be lost, as evidenced by a decrease in muscle weight as well as muscle function.

Denervation and Sarcopenia.

Denervation due to a progressive loss of motoneurons and (i) the lack of re-innervation or (ii) incomplete re-innervation of skeletal muscle fibers during the regular aging process is a contributing factor to sarcopenia, the continuous process of muscle atrophy in the course of regular aging that is characterized by a gradual loss of muscle mass and muscle strength over a span of months and years (Luff, 1998). A regular aging process means herein an aging process that is not influenced or accelerated by the presence of disorders and diseases which promote skeletalmuscular neurodegeneration.

Denervation and Muscle Disuse.

Denervation is also contemplated a contributing factor to skeletal muscle atrophy that results from extended periods of muscle disuse over the span of days, weeks and months. Muscle strength and muscle size are directly influenced by the extent of muscle use. High physical activity levels where muscles are repeatedly exercised against heavy loads lead to strong and large muscles, while physical inactivity where muscles are 'dis-used' meaning that they are little to not at all exercised over the span of several days, weeks or months leads to weakened and small-sized muscles. In this context, skeletal muscle atrophy can result from skeletal muscle disuse in subjects as a consequence of a skeletomuscular injury when the muscle needs to be rested for full recovery or when the muscle needs to be immobilized by means of, e.g., a cast over a time period of days, weeks or even months. Skeletal muscle atrophy can also result from muscle restriction due to surgery, as it can be in the case of spinal fusion surgeries (Hu et al., 2006). Atrophy of the diaphragm muscles in subjects was also reported following 1-3 days of diaphragm inactivity in the context of mechanical ventilation (Levine et al., 2008). Other reasons for skeletal muscle atrophy are joint immobilization, steroid treatment, sepsis, cancer, metabolic disorders and hyperthyroidism (Jagoe & Goldberg, 2001).

Muscle Atrophy and the Involvement of the Ubiquitin-Proteasome Pathway

Muscle atrophy occurs when the physiological balance between protein synthesis and protein degradation is disturbed and more protein is degraded than synthesized. Activation of the ATP-dependent ubiquitin-proteasome pathway is known to play a major role in the increased loss of muscle protein by attaching ubiquitin (Ub), a small, 76 amino acid heat-stable protein, to particular proteins for rapid degradation via a proteasome (Glickman & Ciechanover, 2002). Loss of nerve supply to muscle fibers (denervation) results in muscle atrophy mainly due to excessive proteolysis mediated by the ubiquitin-proteosome pathway in many pathological states that include fasting, metabolic acidosis, muscle denervation, kidney failure, cachexia, uremia, diabetes mellitus, sepsis, AIDS wasting syndrome, burns and Cushing's syndrome (Beehler et al., 2006). The activity status of the ubiquitin-proteasome pathway can be determined by assessing the various enzymes that are involved in the ubiquitination process, including E1 ubiquitin-activating enzymes, E2 ubiquitin-conjugating enzymes and E3 ubiquitin-protein ligases such as atrogin-1 (atrogin) and MuRF1 (Muscle RING Finger 1).

Assessing Muscle Atrophy

Muscle force is proportional to the cross-sectional area (CSA), and muscle velocity is proportional to muscle fiber length. Thus, comparing the cross-sectional areas and muscle fibers between various kinds of muscles can provide an indication of muscle atrophy. Various methods are known in the art to measure muscle strength and muscle weight, see, for example, "Musculoskeletal assessment: Joint range of motion and manual muscle strength" by Hazel M. Clarkson, published by Lippincott Williams & Wilkins, 2000. The production of tomographic images from selected muscle tissues by computed axial tomography is another way of measuring muscle mass, and also sonographic evaluation.

Muscle Atrophy Resulting from Traumatic Nerve Injury and Neurodegenerative Motoneuron Diseases Muscle atrophy severely affects the quality of life, as the concerned individuals are impaired or even incapable of performing tasks that involve lifting, walking or running. In motoneuron diseases, the information transmission from motor neurons in the spinal cord to skeletal muscle fibers via somatic motor nerve fibers is impaired or fully interrupted. Motor neurons and muscle fibers interface at the neuromuscular junction. Upon stimulation in vertebrates, the motor neuron releases neurotransmitters that bind to postsynaptic receptors and trigger an excitatory, i.e. contractile, response in the muscle fiber. Since, thus, the contraction of a skeletal muscle can only be prompted through the firing of motor neurons with the transmission of a nerve impulse, an interruption of that transmission means that the skeletal muscle becomes inactive and atrophic over time. The interruption of nerve function can occur in the brain, spinal cord, or a peripheral nerve.

Traumatic Nerve injury. A traumatic nerve injury is a nondegenerative, noncongenital insult to the upper and/or lower motor neurons afflicted from an external mechanical force, possibly leading to permanent or temporary destruction of those motor neurons.

Motoneuron diseases. Motoneuron diseases are neurological disorders that selectively and irreversibly destroy motoneurons, the cells that control voluntary muscle activity such as speaking, walking, breathing, swallowing and general movement of the body. Motoneuron diseases are primarily inherited and occur in children as well as adults; they are classified in accordance to whether they affect upper motor neurons, lower motor neurons or both. Motoneuron diseases are generally progressive in nature, and cause gradually increasing disability and death.

Amyotrophic lateral sclerosis. Amyotrophic lateral sclerosis (Lou Gehrig's Disease; ALS) is considered the most common form of a motoneuron disease with an onset in adult age of, in average, about 50-60 years and an incidence of 1:50,000 per year. The most common familial forms of ALS in adults are caused by mutations of the superoxide dismutase gene, or SOD1, located on chromosome 21. ALS is a progressive disease with a fatal outcome due to gradual paralysis of all voluntary muscles throughout the body, whereby the breathing and swallowing muscles become affected early on already.

Progressive muscular atrophy. Progressive muscular atrophy is characterized by a progressive degeneration of the lower motor neurons and often times develops into amyotrophic lateral sclerosis. Primary lateral sclerosis. In the case of primary lateral sclerosis (PLS), the upper motor neurons that innervate the muscles in the arms, legs and face gradually degenerate, causing the movements to become very slow and difficult to carry out. While PLS is not fatal, it greatly affects the quality of life. Spinal muscular atrophy. Spinal muscular atrophy (SMA) encompasses a group of inherited diseases of differing gravity that are characterized by progressive and eventually fatal muscle wasting and weakness. The more severe forms of SMA, such as the Werdnig-Hoffman disease, can be present from birth on. The affected babies have very little muscle tone, weak muscles and serious feeding and breathing difficulties. The less severe forms may start in childhood or early adolescence and slowly worsen. The mildest form of SMA starts in adulthood, but all forms of SMA lead eventually to a premature death. Post-polio syndrome (PPS). Post-polio syndrome is a form of muscular atrophy that gradually develops in individuals who had been infected with the poliovirus many years earlier and had enjoyed a disease-free period of prolonged stability which can span several decades. While the post-polio syndrome is usually not fatal, it greatly affects a person's ability to swallow and to speak; eventually, the post-polio syndrome leads to paralysis.

Progressive bulbar palsy. Progressive bulbar palsy, also called progressive bulbar atrophy, affects the lower motor neurons in the bulb-shaped brain stem that are needed for chewing, swallowing and speaking and eventually leads to a loss of the ability to speak, chew or swallow.

Pseudobulbar palsy. Individuals who suffer from pseudobulbar palsy exhibit the same symptoms as individuals with progressive bulbar palsy, but in the case of pseudobulbar palsy the upper motor neurons, which transmit signals to the lower motor neurons in the brain stem, are degenerated.

All of the described diseases severely impair the quality of life and, in many cases, lead to death due to an ability to breathe. No effective treatment has been developed so far.

Mammalian Target of Rapamycin (mTOR): mTORC1 and mTORC2

The mammalian target of rapamycin (mTOR) is an evolutionary conserved serine/threonine protein kinase, that regulates cell growth and proliferation, and a key component of the phosphoinositide 3-kinase (PI3K)/Akt/mTOR signaling pathway. The PI3K/Akt/mTOR signaling pathway is often activated in human cancers and, therefore, mTOR is also a clinically important target for cancer treatment. The mTOR pathway integrates both extracellular and intracellular signals and acts as a central regulator of cell metabolism, growth, proliferation and survival (Proud, 2009).

mTOR is composed of two distinct molecular complexes, mTOR complex 1 (mTORC1), which is sensitive to inhibition with rapamycin, and mTOR complex 2 (mTORC2), which is not sensitive to inhibition with rapamycin (Hay and Sonenberg, 2004). The mTORC1 and mTORC2 complexes contain shared and distinct partner proteins and control a myriad of cellular processes in response to diverse environmental cues. Each complex contains mTOR, mLST8/GβL, and deptor. mLST8/GβL binds the mTOR kinase domain in both complexes but appears more critical for mTORC2 assembly and signaling. Deptor functions as an inhibitor of both complexes. Other partner proteins distinguish the two complexes. mTORC1 contains exclusively raptor and PRAS40. Raptor functions as a scaffolding protein that links the mTOR kinase with mTORC1 substrates to promote mTORC1 signaling. PRAS40 functions in a regulatory capacity. In contrast, mTORC2 contains exclusively rictor (rapamycin-insensitive companion of mTOR), mSin1, and PRR5/protor. Rictor and mSin1 promote mTORC2 assembly and signaling; the function of PRR5/protor remains unknown.

mTOR complex 1 (mTORC1). mTORC1 consists of at least five components: (i) mTOR, the catalytic subunit of the complex; (ii) Raptor; (iii) mLS8; (iv) PRAS40; and (v) Deptor. mTORC1 exerts its effect on protein translation by phosphorylating the ribosomal S6K1 (protein S6 kinase 1) and 4E-BP1 (eukaryotic translation initiation factor eIF4E binding protein 1) proteins, which regulate growth and protein synthesis, respectively. Phosphorylation of 4EBP by mTORC1 relieves its inhibition on translation initiation and plays a major role in mTORC1-dependent translation regulation (Thoreen et al., 2012; Hsieh et al., 2012), as does activation of S6K by mTORC1 (Lee et al., 2007). Tuberous sclerosis complex 1 (TSC1) is an upstream inhibitor of mTORC1 whose deletion leads to hyperactive mTORC1.

Rapamycin and its analogs, so called rapalogs such as temsirolimus and everolimus, inhibit phosphorylation of S6K1 and 4E-BP1 through allosteric inhibition of mTORC1 (Serini et al., 1998).

During muscle development, mTORC1 activity appears to be essential for maintenance of muscle mass. Inhibition of mTORC1 activity in normally innervated muscle through either genetic deletion of the mTORC1 component, raptor (Bentzinger et al., 2006), or overexpression of the mTORC1 inhibitor, TSC1 (Wan et al., 2006), causes muscle atrophy (Aguilar et al., 2007); Mieulet et al., 2007). Similarly, activation of mTORC1 by overexpression of constitutively active Akt, an upstream activator of mTORC1, has been reported to induce muscle hypertrophy (Bodine et al., 2001b). These experiments clearly show that mTORC1 activity is required for building up muscle mass during development. However, the functional role of mTORC1 in adult mature muscle remains unclear.

mTOR complex 2 (mTORC2). mTORC2 is insensitive to rapamycin treatment and is known to function as a regulator of the cytoskeleton. mTORC2 consists of six different known proteins: (i) mTOR; (ii) Rictor; (iii) mSIN1; (iv) Protor-1; (v) mLST8; and (vi) Deptor.

Forkhead Box O Protein Family

The FoxO proteins are a subgroup of the forkhead family of transcription factors, which is characterized by a conserved DNA-binding domain, the so-called forkhead box or Fox. Members of the "O" class, the FoxO proteins, are regulated by the insulin/PI3K/Akt signaling pathway and are well-known upstream regulators of the muscle-specific E3 ubiquitin ligases, atrogin and MuRF1. The overexpression of FoxO proteins induces atrogin and MuRF1 expression and results in muscle atrophy (Sandri et al., 2004; Kamei et al., 2004). Specific inhibition of FoxO function with dominant negative forms of FoxO preserves rat soleus muscle from immobilization-induced muscle atrophy (Senf et al., 2010) and also reduces muscle wasting in cancer cachexia and sepsis (Reed et al., 2011).

Inhibitors of Mammalian Target of Rapamycin (mTOR Inhibitors) for Decreasing the Activity of Mammalian Target of Rapamycin The present invention provides methods for treating denervation-induced muscle atrophy due to traumatic nerve injury or motoneuron diseases by the administration of molecules that inhibit the mammalian target of rapamycin (mTOR), particularly mTORC1.

The inventors of the present invention have found that the inhibition of mTORC1 with rapamycin prevents muscle atrophy in denervated skeletal muscles of mice. As described in the Examples section, infra, the administration of an mTORC1 inhibitor, such as rapamycin, significantly prevented denervation-induced muscle atrophy in mice, as evidenced by a significant decrease in muscle weight loss when compared to control mice without the treatment with an mTORC1 inhibitor. The results indicate that a composition comprising an agent that inhibits mTORC1, such as rapamycin, is useful to attenuate muscle atrophy and to attenuate muscle weight loss. It is also contemplated that denervation-induced muscle atrophy may be prevented by administering molecules that are inhibitors of mTOR.

In some embodiments, such molecules are mTORC1 inhibitors such as rapamycin. In other embodiments, such molecules are dual mTORC1/mTORC2 inhibitors.

The inventors have also shown, as explained in the Examples section, infra, that denervation-activated mTORC1 activates E3 ubiquitin ligases by modulating the Akt-FoxO cascade: denervation-activated mTORC1 inhibits Akt activity, which activates FoxO proteins and, thus, effects muscle atrophy. Akt normally prevents the expression of muscle atrophy-induced ubiquitin ligases by inhibiting the FoxO transcription factors (Stitt et al., 2004). In addition to the novel understanding of mTORC1 function, the inventors have also shown that complete deletion of the FoxO proteins (FoxO 1, 3 and 4) in skeletal muscle (i) induces resistance of denervation muscle atrophy and (ii) causes hypertrophy in normal, innervated muscle.

Taken together, denervation-induced muscle atrophy, as resulting from traumatic nerve injury or motor neuron diseases, can be attenuated or prevented by the inhibition of mTOR, particularly of mTORC1, and the inhibition/inactivation of FoxO proteins 1, 3 and 4.

mTORC1 Inhibitors

Rapamycin.

Rapamycin, a bacterial macrolide-derived molecule, interacts with the cellular protein FKBP12, and this complex directly binds to the mTOR FKBP12-rapamycin-binding (FRB) domain to allosterically inhibit mTORC1. As an allosteric inhibitor, rapamycin weakens the interaction between mTOR and raptor (regulatory associated protein of mTOR), an mTORC1 regulatory partner, and reduces mTORC1 intrinsic kinase activity. Chronic high-dose rapamycin inhibits mTORC2 signaling in certain cell types by impeding mTORC2 assembly.

Rapamycin and its analogs (rapalogs) such as temsirolimus and everolimus are allosteric inhibitors of mTORC1 and do not affect mTORC2. While rapamycin and analogs are effective inhibitors of mTORC1, they might not block mTORC1 entirely (Choo et al., 2008).

ATP Competitive (Dual) mTORC1/mTORC2 INHIBITORS

ATP competitive inhibitors such as OSI-027, AZD-8055, and WYE-132, all small molecules, suppress both mTORC1 and mTORC2 functions. Other mTOR inhibitors include small molecules such as deforolimus, temsirolimus.

Forkhead Box Transcription Factors (FoxO) Inhibitors=Agents that Decrease the Activity of at Least One of Forkhead Box Transcription Factors 1, 3 and 4

There are currently no small molecules identified that inhibit FoxO 1, 3 and 4, as described herein. The inventors currently achieve blocking of the DNA binding sites of FoxO 1, 3 and 4 with FoxO-DNA-binding human dominant negative FoxO-TAT fusion proteins (SEQ ID NOS 1 and 2), as depicted in FIG. 6.

Identification of mTOR and FoxO Inhibitors

Further mTOR and FoxO inhibitors may be biologically active, recombinant, isolated peptides and proteins, including their biologically active fragments, peptidomimetics or small molecules. In the working examples, rapamycin was utilized to block mTORC1.

mTOR and FoxO inhibitors may be identified experimentally using a variety of in vitro and/or in vivo models. Isolated mTOR and FoxO inhibitors can be screened for binding to various sites of the purified mTOR and FoxO proteins, respectively.

mTOR and FoxO inhibitors typically are organic molecules, preferably small organic compounds having a molecular weight of more than 50 and less than about 2,500 daltons. They may comprise functional groups necessary for structural interaction with proteins (e.g., hydrogen bonding), and typically include at least an amine, carbonyl, hydroxyl, or carboxyl group. They often comprise cyclical carbon or heterocyclic structures and/or aromatic or polyaromatic structures substituted with one or more functional groups.

mTOR and FoxO inhibitors may also be synthesized or isolated from natural sources (e.g., bacterial, fungal, plant, or animal extracts). The synthesized or isolated candidate compound may be further chemically modified (e.g., acylated, alkylated, esterified, or amidified), or substituents may be added (e.g., aliphatic, alicyclic, aromatic, cyclic, substituted hydrocarbon, halo (especially chloro and fluoro), alkoxy, mercapto, alkylmercapto, nitro, nitroso, sulfoxy, sulfur, oxygen, nitrogen, pyridyl, furanyl, thiophenyl, or imidazolyl substituents) to produce structural analogs, or libraries of structural analogs (see, for example, U.S. Pat. Nos. 5,958,792; 5,807,683; 6,004,617; 6,077,954). Such modification can be random or based on rational design (see, for example, Cho et al., 1998; Sun et al., 1998).

mTOR and FoxO inhibitors may be administered, orally, locally or systemically, in a dosage and dosage regimen that is effective to provide the desired effect of attenuating or preventing skeletal muscle atrophy in denervated skeletal muscles.

Dosages, Dosing Regimens, Formulations and Administration of mTOR and FoxO Inhibitors The dosage and dosing regimen for the administration of mTOR and FoxO inhibitors to attenuate or prevent skeletal muscle atrophy in denervated skeletal muscles, as provided herein, is selected by one of ordinary skill in the art, in view of a variety of factors including, but not limited to, age, weight, gender, and medical condition of the subject, the severity of the inflammatory response that is experienced, the route of administration (oral, systemic, local including nasal), the dosage form employed, and may be determined empirically using testing protocols, that are known in the art, or by extrapolation from in vivo or in vitro tests or diagnostic data.

The dosage and dosing regimen for the administration of mTOR and FoxO inhibitors, as provided herein, is also influenced by toxicity in relation to therapeutic efficacy. Toxicity and therapeutic efficacy can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Molecules that exhibit large therapeutic indices are generally preferred.

The therapeutically effective dose of mTOR and FoxO inhibitors can, for example, be less than 50 mg/kg of subject body mass, less than 40 mg/kg, less than 30 mg/kg, less than 20 mg/kg, less than 10 mg/kg, less than 5 mg/kg, less than 3 mg/kg, less than 1 mg/kg, less than 0.3 mg/kg, less than 0.1 mg/kg, less than 0.05 mg/kg, less than 0.025 mg/kg, or less than 0.01 mg/kg. Therapeutically effective doses of mTOR and FoxO inhibitors, administered to a subject as provided in the methods herein can, for example, can be between about 0.001 mg/kg to about 50 mg/kg. In certain embodiments, the therapeutically effective dose is in the range of, for example, 0.005 mg/kg to 10 mg/kg, from 0.01 mg/kg to 2 mg/kg, or from 0.05 mg/kg to 0.5 mg/kg. In various embodiments, an effective dose is less than 1 g, less than 500 mg, less than 250 mg, less than 100 mg, less than 50 mg, less than 25 mg, less than 10 mg, less than 5 mg, less than 1 mg, less than 0.5 mg, or less than 0.25 mg per dose, which dose may be administered once, twice, three times, or four or more times per day. In certain embodiments, an effective dose can be in the range of, for example, from 0.1 mg to 1.25 g, from 1 mg to 250 mg, or from 2.5 mg to 1000 mg per dose. The daily dose can be in the range of, for example, from 0.5 mg to 5 g, from 1 mg to 1 g, or from 3 mg to 300 mg.

In some embodiments, the dosing regimen is maintained for at least one day, at least two days, at least about one week, at least about two weeks, at least about three weeks, at least about one month, three months, six months, one year, three years, six years or longer. In some embodiments, an intermittent dosing regimen is used, i.e., once a month, once every other week, once every other day, once per week, twice per week, and the like.

mTOR and FoxO inhibitors or pharmaceutical compositions containing mTOR or FoxO inhibitors may be administered to a subject using any convenient means capable of resulting in the desired attenuation or prevention of skeletal muscle atrophy. Routes of administration of mTOR or FoxO inhibitors or pharmaceutical compositions containing mTOR or FoxO inhibitors include, but are not limited to, oral, nasal and topical administration and intramuscular, subcutaneous, intravenous, or intraperitoneal injections. mTOR or FoxO inhibitors or pharmaceutical compositions containing mTOR or FoxO inhibitors may also be administered locally at the site of skeletal muscle atrophy.

mTOR or FoxO inhibitors may be administered in a single daily dose, or the total daily dose may be administered in divided doses, two, three, or more times per day. Optionally, in order to reach a steady-state concentration in the target tissue quickly, an intravenous bolus injection of mTOR or FoxO inhibitors can be administered followed by an intravenous infusion of the mTOR or FoxO inhibitor.

mTOR or FoxO inhibitors can be administered to the subject as a pharmaceutical composition that includes a therapeutically effective amount of a mTOR or FoxO inhibitor in a pharmaceutically acceptable vehicle. It can be incorporated into a variety of formulations for therapeutic administration by combination with appropriate pharmaceutically acceptable carriers or diluents, and may be formulated into preparations in solid, semi-solid, liquid, or gaseous forms, such as tablets, capsules, powders, granules, ointments, solutions, suppositories, injections, inhalants, gels, microspheres, and aerosols.

In some embodiments, a mTOR or FoxO inhibitor can be formulated as a delayed release formulation. Suitable pharmaceutical excipients and unit dose architecture for delayed release formulations may include those described in U.S. Pat. Nos. 3,062,720 and 3,247,066. In other embodiments, the mTOR or FoxO inhibitor can be formulated as a sustained release formulation. Suitable pharmaceutical excipients and unit dose architecture for sustained release formulations include those described in U.S. Pat. Nos. 3,062,720 and 3,247,066. mTOR or FoxO inhibitors can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly($\epsilon$-caprolactone) and poly(alkylene oxide) (U.S. 20030068384) to create a sustained release formulation. Such formulations can be used in implants that release an agent over a period of several hours, a day, a few days, a few weeks, or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 9726015, WO 97/04744, and. US20020019446. In such sustained release formulations microparticles of drug are combined with microparticles of polymer. Additional sustained release formulations are described in WO 02/38129, EP 326 151, U.S. Pat. No. 5,236,704, WO 02/30398, WO 98/13029; U.S. 20030064105, U.S. 20030138488A1, U.S. 20030216307A1, U.S. Pat. No. 6,667,060, WO 01/49249, WO 01/49311, WO 01/49249, WO 01/49311, and U.S. Pat. No. 5,877,224.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients, and the like. The compositions can also include additional substances to approximate physiological conditions, such as pH adjusting and buffering agents, toxicity adjusting agents, wetting agents, and detergents. The composition can also include any of a variety of stabilizing agents, such as an antioxidant for example. Tablet formulations can comprise a sweetening agent, a flavoring agent, a coloring agent, a preservative, or some combination of these to provide a pharmaceutically elegant and palatable preparation.

Further guidance regarding formulations that are suitable for various types of administration can be found in Remington's Pharmaceutical Sciences, Mace Publishing Company, Philadelphia, Pa., 20th ed. (2000).

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in-vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

EXPERIMENTAL PROCEDURES

The following methods and materials were used in the examples that are described further below.

Animals.

The animal care and experimental procedures followed the protocol approved by the University of Michigan Committee on Use and Care of Animals (UCUCA) and VA Palo Alto Healthcare System Institutional Animal Care and Use Committee (IACUC). NSA (CF-1) mice were purchased from Harlan. The generation of TSC1lox/lox mice with exons 17 and 18 of TSC1 flanked by loxP sites by homologous recombination has been described (Meikle et al., 2005; Uhlmann et al., 2002). Muscle-specific TSC1 ko mice were generated through breeding TSC1 lox/lox mice (C57BL/6J) with hemizygote MCK-Cre mouse line (FVB, Cre+/−, kind gift from Dr. Dario Alessi, University of Dundee), where Cre is under the control of muscle-specific creatine kinase. Briefly, the TSC lox/lox mice were bred with MCK Cre/+ to obtain a TSC lox/+, Cre/+ line, and then the latter was crossed with TSC1 lox/lox mice to generate a TSC1 lox/lox, Cre/+ line. The F3 generation was acquired by breeding TSC1 lox/lox with TSC lox/lox, Cre/+ line. The offspring was genotyped with Cre primers. The Cre+ mice are TSC1 ko mice, while the Cre− mice were used as same genetic background wild-type control. Genotyping was performed as described before (Inoki et al., 2011).

The generation of FoxO1/3/4 lox/lox mice (FVB) with exon 2 (FoxO1, on chromosome 3), exon 3 (FoxO3, on chromosome 10) and exon 1 (FoxO4, on chromosome X) flanked by loxP sites by homologous recombination was carried out at Harvard Medical School and reported before (Paik et al., 2007).

Figure 7:
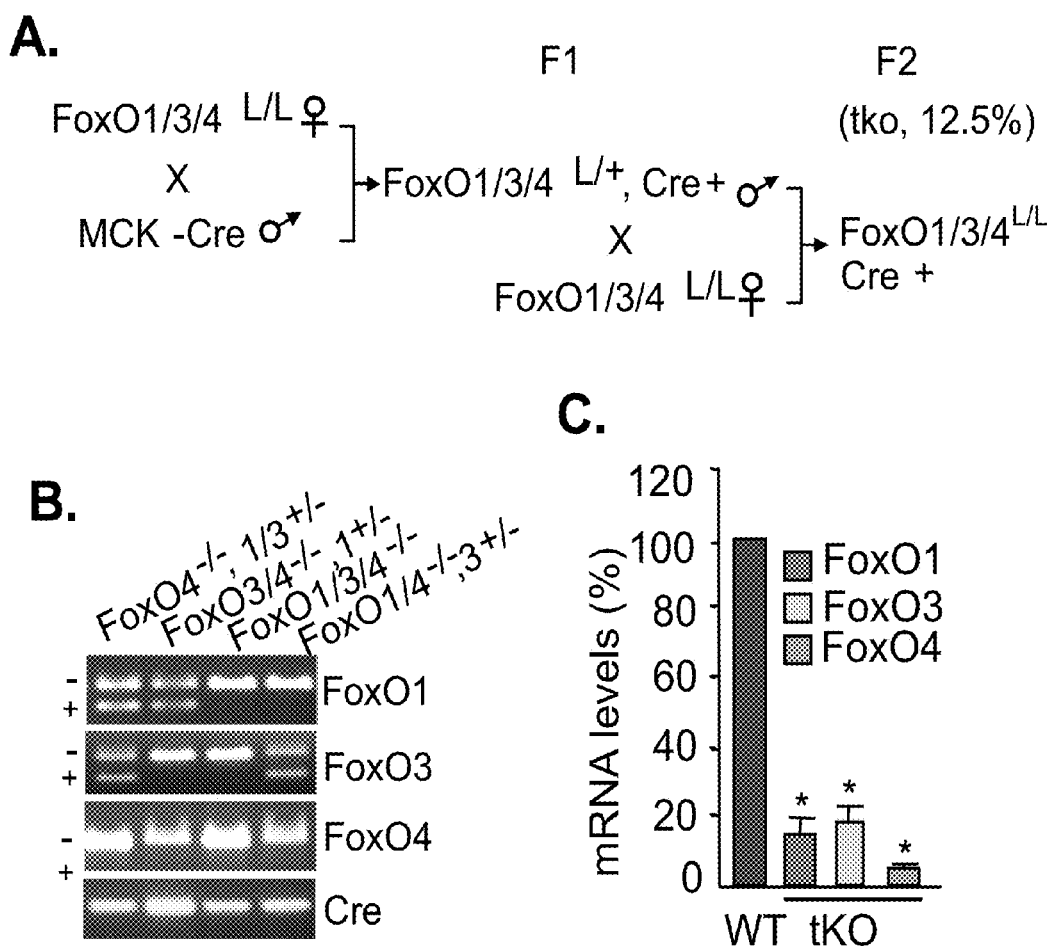
FIG. 7 illustrates the production of a mouse line with muscle-specific triple knockout (TKO) of FoxO1, 3 and 4. A) Mice with floxed FoxO1/3/4 were bred with MCK-Cre mice to generate FoxO1/3/4 L/L, Cre+ F2 mice, which lack FoxO1, 3 and 4. The Cre– F2 counterparts (FoxO L/L, Cre–) serve as control. B) Genotyping results established successful triple FoxO KO. Genomic DNA was extracted and PCR was performed with specific primers. "–" indicates that the PCR product contains the inserted loxp sites, whereas "+" indicates that loxp sites are not detected. C) mRNA abundance of FoxO1, 3 and 4 were measured with realtime PCR in FoxO TKO muscle. Note that the expression of FoxO1, 3, and 4 is significantly reduced, indicating a successful knockout of the specific genes (n=4 mice per genotype, *p<0.5).

FoxO1/3/4 lox/lox female mice were bred in a muscle-specific manner with MCK-Cre (FVB, Jackson lab) male mice (see FIG. 7A) and generated F1 offspring with the genotype of FoxO1/3/4 lox/−, Cre+/−(~50%). Male mice of FoxO1/3/4 lox/−, Cre+/− were then bred with female FoxO1/3/4 lox/lox to generate F2 offspring with the genotype of FoxO1−/−, 3−/−, 4−/− (~12.5%) as well as other intermediates offspring with genotypes at FoxO1+/−, 3+/−, 4−/− (~12.5%), FoxO1−/−, FoxO3+/−, FoxO4−/− (~12.5%), FoxO1+/−, FoxO3+/−, FoxO4−/− (~12.5%) and 50% of Cre− with various combination of floxed FoxO1/3/4. These Cre+, FoxO1/3/4 floxed (FoxO1−/−, 3−/−, 4−/−) mice were further bred with FoxO1/3/4 floxed mice to generate Cre+ (~50%, FoxO tko) and Cre− (~50%, control) FoxO1/3/4 floxed mice. Successful deletion of all 3 FoxO isoforms was confirmed, as described in FIGS. 7B & 7C.

The Cre− mice were used as same genetic background wild-type control. The genotyping primers used were described before (Paik et al., 2007). Primers are listed in table 1.

TABLE 1

Primers

| Genotyping primers | Sequences (5' to 3') |
|---|---|
| Cre-F | GCTCGACCAGTTTAGTTACCC |
| Cre-R | TCGCGATTATCTTCTATATCTTCAG |
| For FoxO1 | |
| oFK1ckA | GCTTAGAGCAGAGATGTTCTCACATT |
| oFK1ckB | CCAGAGTCTTTGTATCAGGCAAATAA |
| oFK1ckD | CAAGTCCATTAATTCAGCACATTGA |
| For FoxO3 | |
| oFK2ckA | ATTCCTTTGGAAATCAACAAAACT |
| oFK2ckB | TGCTTTGATACTATTCCACAAACCC |
| oFK2ckD | AGATTTATGTTCCCACTTGCTTCCT |
| For FoxO4 | |
| oAFXckD | CTTCTCTGTGGGAATAAATGTTTGG |
| oAFXckE | CTACTTCAAGGACAAGGGTGACAG |
| oAFXckM | TGAGAAGCCATTGAAGATCAGA |
| Realtime PCR primers For cDNAs | |
| myogenin-F | ATCTCCGCTACAGAGGCGGG |
| myognein-R | TAGGGTCAGCCGCGAGCAAA |
| HDAC4-F | AGAGAGTGCTGTGCCGAGCA |
| HDAC4-R | ACGGGGTGGTTGTAGGAGGC |
| Atrogin-F | CAACATTAACATGTGGGTGTAT |
| Atrogin-R | GTCACTCAGCCTCTGCATG |
| MuRF1-F | GAGAACCTGGAGAAGCAGCT |
| MuRF1-R | CCGCGGTTGGTCCAGTAG |
| actin-gamma R | CCATCTAGAAGCATTTGCGGTGGACG |
| actin-gamma F | ACCCAGGCATTGCTGACAGGATGC |
| TSC1-F | GTCAATGAGCTGTACCTGGA |
| TSC1-R | CTTTGGTTCTGCTGGAGAAG |
| FoxO1-F | CGCGCAAGACCAGCTCGT |
| FoxO1-R | TCCGCTCTTGCCTCCCTCTG |
| FoxO3-F | GGATAAGGGCGACAGCAACAGC |
| FoxO3-R | GCCTCGGCTCTTGGTGTACTTG |
| FoxO4-F | GGAGAAGCGGCTGACACTCG |
| FoxO4-R | CTTGCCAGTGGCCTCGTTGT |

Denervation by Sciatic Nerve Injury and In Vivo Rapamycin Administration in Mice.

Sciatic nerve injury was performed in an animal operation room with aseptic techniques as described before (Tang et al., 2006). Briefly, adult mice (~8 weeks) were anesthetized with ketamine (100 mg/kg) and xylazine (10 mg/kg). After removing hair, the local skin was disinfected with betadine and 75% ethanol. A small incision was made at mid-thigh level and nerve trunk of the size of about 0.5 cm was removed while the animal was under deep anesthesia, leading to denervation of the lower limb muscles. Animals were then under intensive care until sample collection.

Rapamycin (LC Laboratories; Woburn, Mass.) was initially dissolved in 100% ethanol, stored at −20° C., and further diluted in an aqueous solution of 5.2% Tween 80 and 5.2% PEG 400 (final ethanol concentration, 2%) immediately before use (Wendel et al., 2004). Denervated NSA mice (male, 40 g) were injected immediately with rapamycin i.p. at 1.5 mg/kg, or 6 mg/kg body weight, every other day. Control mice were injected with vehicle with the same amount of ethanol solvent with rapamycin group (6 mg·kg). Muscle samples were collected 15 days later. Muscle wet weight was recorded immediately. For immunostaining, muscles were frozen in OCT in dry ice-cold isopentane. For RNA and protein extraction, muscles were quickly frozen in liquid nitrogen. Student t-test was used to evaluate the statistical significance. P<0.05 was considered as statistically significant. Each of these experiments were performed such that there were 3 to 6 separate experimental mice (for each genotype, dose, and time-point) and 3-6 separate control mice per experiment.

Protein and mRNA Expression.

Protein expression and protein phosphorylation were detected by Western blotting analysis following standard procedures. Antibodies against TSC1, FoxO1, pFoxO1, S6, pS6, Akt, pAkt, ubiquitin were purchased from Cell Signaling, and antiactin was from Santa Cruz. Gene expression levels were detected by Real-time PCR. One ug RNA was reverse transcribed with oligo(dT) primer and SuperScript II (Invitrogen), and 1/20 of the cDNA mixture served as template for PCR reactions. Real-time PCR was performed on an ABI 7900HT by using SYBR Green MasterMix (ThermoFisher Scientific). The primers are listed in Table 1.

Muscle Immunostaining and Cross-Section Area (CSA) Measurements.

Freshly frozen muscle samples were sectioned on cryostat with 14 µm thickness. Stanford procedure was used to perform the immunostaining against FoxO1. DAPI and WGA-Alexa Fluor 488 were purchased from invitrogen. Slides were mounted in Prolong Gold anti-fading reagent (Invitrogen) and imaged by confocal fluorescent microscopy (LSM710, Zeiss). Muscle CSA were measured on WGA-stained muscle cross sections. Three different regions from single section (~200-300 cells/image), 3 consecutive sections were processed. CSA was measured with Fiji, an enhanced version of Image J (http://fiji.sc/wiki/index.php/Fiji). Detail procedure is available upon request. Student t-test was used to evaluate the statistical significance. P<0.05 was considered as statistically significant.

Gene Electrotransfer to Skeletal Muscle.

Gene electrotransfer was performed as previously described (14). Briefly, 20 ug of control plasmid pcDNA3.1 and pcDNA3.1-FoxO-DN were electroporated by injection into TA muscles with a Hamilton syringe, followed by 8 electrical pulses with a duration 60 ms with 100 ms interval with an ECM830 electroporator (BTX). The electrical field intensity was 150 V/cm. The FoxO-DN construct was generated by cloning a cDNA fragment flanking the DNA binding domain (DBD) and nuclear localization signal (NLS) into Topo-pcDNA3.1 vector. PCR primers used for the cDNA amplification are: forward, gccgccgctgggc-cgctcgcggg and reverse, tcaggcagctcggcttcggctcttagcaaa.

PLD Activity and PA Concentration Assays.

Phospholipase D (PLD) and phosphatidyl acid (PA) assay kits were purchased from Cayman Chemical (Ann Arbor, Mich.). The assay was performed by following the supplier's instructions. Protein input was 12 ug/well. Samples were loaded onto 96-well plate and the fluorescence was read by a SpectraMax M2 (Molecular Devices), with excitation wavelength 530-540 nm and emission wavelength 585-595 nm.

I. Methods of Attenuating (or Preventing Before Development of) Skeletal Muscle Atrophy in a Mammalian Subject Suffering from Denervation-Induced Skeletal Muscle Atrophy by Administering a Composition Comprising an Agent that Decreases Activity of Mammalian Target of Rapamycin In one aspect, the present invention provides methods of attenuating (preventing) skeletal muscle atrophy in a mammalian subject, comprising administering to said subject suffering from denervation-induced skeletal muscle atrophy a composition comprising an agent that decreases activity of mammalian target of rapamycin (mTOR) in a dosage and dosing regimen effective to attenuate, i.e. decrease or reverse, denervation-induced skeletal muscle atrophy.

Denervation-induced skeletal muscle atrophy refers to the loss of muscle tissue and/or loss of muscle function which can result from (i) a neurodegenerative motoneuron disease such as pseudobulbar palsy or progressive bulbar palsy, post-polio syndrome, progressive muscular atrophy, primary lateral sclerosis, spinal muscular atrophy, amyotrophic lateral sclerosis, (ii) a traumatic nerve injury, (iii) aging-induced sarcopenia or muscle disuse due to immobilization and similar circumstances.

In the following, examples 2, 5 and 7 describe embodiments in detail, where the administration of an agent that decreases the activity, i.e. the function, of mammalian target of rapamycin such as rapamycin is effective in attenuating denervation-induced skeletal muscle atrophy or even in preventing the development of denervation-induced skeletal muscle atrophy.

II. Methods of Attenuating (or Preventing Before Development of) Skeletal Muscle Atrophy in a Mammalian Subject Suffering from Denervation-Induced Skeletal Muscle Atrophy by Administering a Composition Comprising an Agent that Decreases Activity of at Least One of Forkhead Box Transcription Factors 1, 3 and 4 in a Dosage and Dosing Regimen Effective to Attenuate Denervation-Induced Skeletal Muscle Atrophy In one aspect, the present invention provides methods of attenuating (preventing) skeletal muscle atrophy in a mammalian subject, comprising administering to said subject suffering from denervation-induced skeletal muscle atrophy a composition comprising an agent that decreases activity of at least one of Forkhead Box Transcription Factors 1, 3 and 4 (FoxO 1, 3 and 4) in a dosage and dosing regimen effective to attenuate, i.e. decrease or reverse, denervation-induced skeletal muscle atrophy. Denervation-induced skeletal muscle atrophy was defined above.

In the following, examples 4 and 8 describe embodiments in detail, where the administration of an agent that decreases the activity, i.e. the function, of at least one of Forkhead Box Transcription Factors 1, 3 and 4, such as a human dominant negative FoxO-TAT fusion protein, is effective in attenuating denervation-induced skeletal muscle atrophy or even in preventing the development of denervation-induced skeletal muscle atrophy.

Examples 1, 3 and 6 describe embodiments in detail, where the combined administration of an agent that decreases the activity of mTOR and an agent that decreases the activity of at least one of FoxO1, 3 and 4 may be effective to attenuate, i.e. decrease or reverse, or even prevent the development of denervation-induced skeletal muscle atrophy.

EXAMPLES

The following examples are put forth so as to provide those of ordinary skill in the art with a complete disclosure and description of how to make and use the present invention; they are not intended to limit the scope of what the inventors regard as their invention. Unless indicated otherwise, parts are parts by weight, molecular weight is average molecular weight, temperature is in degrees Centigrade, and pressure is at or near atmospheric.

Example 1 mTORC1-S6K and Akt-FoxO Signaling Pathways are Reciprocally Regulated in Denervated Muscle To investigate the possible involvement of the mTORC1 pathway in denervation muscle atrophy, mTORC1 activity was examined 3 days (designated as early) and 15 days (designated as late) after denervation in normal mouse hindlimb. Three days post-denervation, Western blot analysis indicated that the phosphorylation of some of the components in the mTORC1 pathway, such as mTOR, S6K and S6, was moderately increased, indicating a mild activation of mTORC1 pathway, whereas the phosphorylation and activity of Akt and FoxO1 remained unchanged (FIG. 1A, left panels). In muscle 15 days after denervation, the phosphorylation of mTORC1 and of two of its downstream effectors (S6K and S6) was markedly increased. At this later time point, the phosphorylation of Akt and FoxO1 was reduced compared to that in innervated muscle (FIG. 1A, right panels). The total protein abundance of the mTORC1 components mTOR and raptor were also increased following denervation, indicating that activation of mTORC1 by denervation could result from both the induction of phosphorylation of mTOR and the increased abundance of mTORC1 components (FIG. 1A). Quantitation confirmed a reciprocal regulatory pattern between the activity of the mTORC1 pathway, represented by the ratio of phosphorylated S6K to total S6K, and the activity of Akt-FoxO cascade, represented by the ratio of phosphorylated Akt to total Akt and phosphorylated FoxO1 to FoxO1 (FIG. 1B). Furthermore, immunostaining on cryosections of innervated and denervated muscles indicated that mTORC1 activity, as assessed by phosphorylated S6, was increased in skeletal muscle fibers following denervation (FIG. 1C). Additionally, we observed that FoxO1 protein accumulated in nuclei of muscle fibers 15 days after denervation, consistent with a reduction in Akt activity that leads to decreased phosphorylation of FoxO1 and its relocation into myonuclei (FIG. 1D). Together, these data show that denervation activates the mTORC1-S6K pathway, suppresses Akt activity, and activates FoxO.

Example 2

Constitutively Active mTORC1 Sensitizes Muscle to, Rather than Prevents, Denervation-Induced Skeletal Muscle Atrophy Because mTORC1 activation is thought to generally increase protein synthesis (Bodine et al., 2001b; Wang & Proud, 2006), the inventors of the present application hypothesized initially that the induction of mTORC1 activity in denervated muscle would serve as a compensatory mechanism directed toward preventing muscle atrophy. To test this concept, a mouse model of mTORC1 overactivity was established by deleting the endogenous mTORC1 inhibitor, TSC1, in a muscle-specific manner. Specifically, as described supra under Experimental Procedures, muscle-specific TSC1 KO mice were generated by breeding floxed TSC1 mice (TSC1L/L) with MCK-Cre mice, where Cre was under the control of muscle-specific creatine kinase. The Cre– counterparts served as control.

Figure 2:
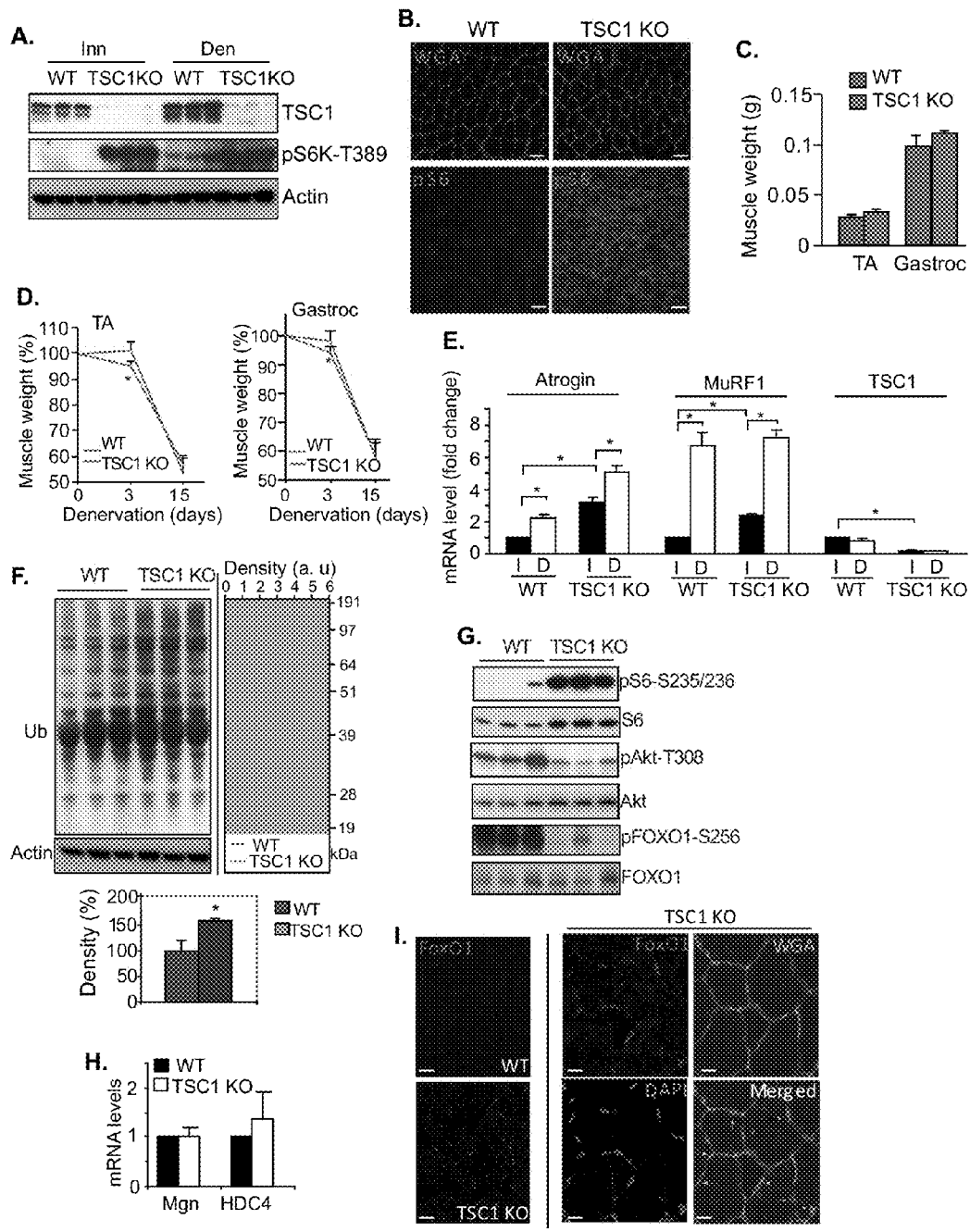
FIG. 2 illustrates that activated mTORC1 does not prevent denervation skeletal muscle atrophy but rather activates FoxO and increases expression of ubiquitin E3 ligase genes. A) Activation of the mTORC1 pathway in gastrocnemius muscle of TSC1 KO mice as determined by phosphorylation of S6K protein (n=3 mice per genotype and treatment). Inn: innervated; Den: denervated. B) Cross-sections of TA muscle stained by WGA or for phosphorylated S6. Scale bar, 50 μm. Images are representative of 3 mice per genotype. C) Muscle weight of wild-type and TSC1 KO mice at 8 weeks of age. TA, tibialis anterior, Gastroc, Gastrocnemius (n=4 mice per genotype). D) Whole muscles (TA and Gastrocnemius) were weighed following 3 and 15 days denervation and normalized to their contralateral, innervated counterparts (n=4 mice per genotype, *p<0.05). E) mRNA expression of E3 ubiquitin ligases in innervated and denervated gastrocnemius muscles from WT and TSC1 KO mice. Results are normalized to γ-actin expression (n=4 mice per genotype, *p<0.05). F) Total protein extracts from gastrocnemius muscles were immunoblotted with anti-ubiquitin (ub) antibody. Actin was used as the loading control. Gray density was plotted as a continuous function on the right panel, and mean density of detectable ubiquitinated proteins is shown in the lower panel (n=3 mice per genotype, *p<0.05). G) Protein extracts from gastrocnemius muscles were immunoblotted with the indicated antibodies. n=3 mice per genotype. H) mRNA expression of HDAC4 and myogenin was normalized to that of γ-actin. (n=3 mice per genotype). I) Cryosections of TA muscle from WT and TSC1 KO mice were stained with anti-FoxO1 (red), DAPI (blue) and WGA (green), and the images merged to show the myonuclear localization of FoxO1. Scale bar, 15 μm. Images are representative of 3 mice per genotype.

As can be seen in FIGS. 2 A, B & E, the resulting TSC1 KO mice showed increased mTORC1 activity in skeletal muscle fibers, as indicated by the presence of phosphorylated S6 (pS6). At young adult age (6 to 8 weeks), the TSC1 KO mice appeared phenotypically normal, without noticeable differences in muscle morphology or mass compared to that of wild-type mice (FIGS. 2A & C). However, at three days after denervation by sciatic nerve injury, the TSC1 KO mice exhibited muscle atrophy, suggesting that increased mTORC1 activity sensitized skeletal muscle to denervation-induced atrophy (FIG. 2D). The expression of atrophy-associated genes, such as those encoding atrogin and MuRF1, were induced to a greater extent by denervation in TSC1 KO mice compared to wild-type mice (FIG. 2E), suggesting that mTORC1 activation may play a role in activating the E3 ligase-mediated protein degradation pathway.

Example 3

Constitutively Active mTORC1 is Sufficient to Activate FoxO and the Ubiquitin-Proteasome System by Suppressing Akt in Skeletal Muscle Consistent with the induction of E3 ubiquitin ligases (FIG. 2E), the extent of protein ubiquitination was also significantly induced in the TSC1 KO skeletal muscle, ~150% of the total protein ubiquitination in wild-type skeletal muscle (FIG. 2F). TSC1 KO muscle showed increased phosphorylation of S6 but reduced phosphorylation of Akt and FoxO1 (FIG. 2G), similar to the phosphorylation patterns in denervated muscle (FIG. 1A). Like FoxO, the HDAC4-myogenin pathway can increase expression of genes encoding E3 ubiquitin ligases (Moresi et al., 2010; MacPherson et al., 2011), but no changes were observed in the gene expression of myogenin or HDAC4 in TSC1 KO muscle (FIG. 2H). Immunostaining revealed that FoxO1 protein accumulated in TSC1 KO muscle and co-localized with nuclei, suggesting that FoxO1 is translocated into myonculei with mTORC1 activation (FIG. 2I). Therefore, increased mTORC1 activity stimulates a denervation-like signaling cascade that accelerates muscle atrophy in response to denervation, although it does not induce muscle atrophy in normal innervated muscle at a young age.

Example 4

Figure 3:
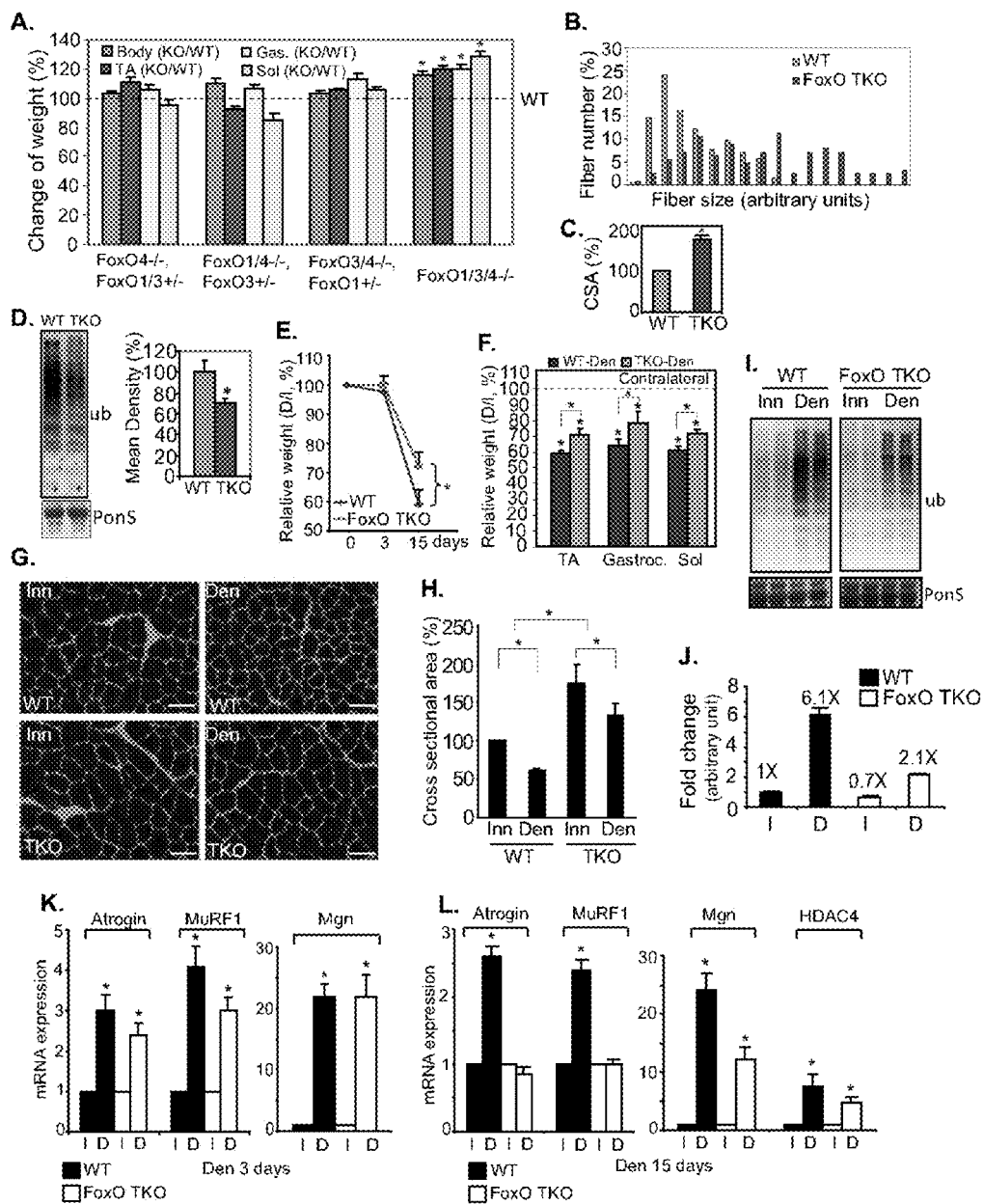
FIG. 3 illustrates that triple deletion of FoxO1, 3, and 4 resulted in muscle hypertrophy and reduced protein degradation and mitigated denervation muscle atrophy. A) TA, soleus, and gastrocnemius muscle and whole body were weighed in WT mice, FoxO TKO mice, and breeding intermediates. The results for WT mice are indicated by the horizontal, dotted line at 100% (n=4 mice per genotype, *p<0.05). B&C) Muscle fiber size in WT and FoxO TKO muscle. B) The distribution of the cross-sectional area of at least 600 TA muscle fibers per specimen. Graph is a representative of n=4 mice per genotype. C) Mean cross-sectional area (CSA) (n=4 mice per genotype, *p<0.05). D) Western blot analysis for protein ubiquitination (anti-ub); Ponceau S-stained total protein was used to show equal loading and to normalize gray density (representative image is shown of n=3 mice per genotype, *p<0.05). E) Time dependent changes in gastrocnemius muscle weight following denervation in WT and FoxO TKO mice (n=4 mice per genotype and treatment, *p<0.05). The weight of the denervated (D) muscle was normalized to its contralateral innervated (I) muscle and results expressed as percentages (D/I). F) Muscle weight loss in TA, soleus and gastrocnemius muscle 15 days after denervation in WT and FoxO TKO mice. The values for contralateral, innervated muscles were set at 100% and indicated by the horizontal line (n=4 mice per genotype and treatment, *p<0.05). G) Cryosections of TA muscles were stained with WGA. Representative images are shown. H) Quantitation of CSA of 800-1000 fibers in each TA muscle (n=4 mice per genotype and treatment, *p<0.05). I) Protein extracts from muscles 15-days after denervation and the contralateral innervated controls were immunoblotted with anti-ubiquitin. Ponceau S staining of total protein is shown as loading control. n=2 mice per genotype and treatment. J) Mean fold changes in the amount of ubiquitinated proteins (total ubiquitinated proteins normalized to total protein stained with Ponceau S) are shown (n=2 mice per genotype and treatment). K&L) mRNA expression of regulatory factors, normalized to that of γ-actin, in gastrocnemius muscles 3-days (K) or 15-days (L) after denervation. Fold changes were calculated by normalizing mRNA in denervated muscles to that in the contralateral controls (n=4 mice per genotype and treatment, *p<0.05).

Lack of Forkhead Box O Transcription Factors (FoxOs) Induces Muscle Fiber Hypertrophy and Resistance to Denervation-Induced Atrophy Because FoxO1 is activated in denervated muscle as well as in muscle with increased mTORC1 activity, and because FoxOs transcriptionally activate the genes encoding the E3 ubiquitin ligases atrogin and MuRF1, FoxOs would appear to be likely downstream mediators of mTORC1-induced atrophy in denervated muscle. The inventors, therefore, generated FoxO knockout mice to determine whether FoxOs are required for denervation-induced muscle atrophy. Because FoxO1, 3 and 4 are present in skeletal muscle and may have overlapping functions, all 3 genes were simultaneously deleted in a muscle-specific manner by breeding floxed FoxO1/3/4 mice with MCK-Cre mice and successful deletion of all 3 FoxO isoforms was confirmed, as further described supra in Experimental Procedures. Adult (8 week old) homozygous FoxO1/3/4 triple knockout mice (FoxO TKO) appeared phenotypically normal, but had significantly higher body weight compared to wild-type mice or the single or double FoxO KO mice (FIG. 3A). The weights of the tibialis anterior, gastrocnemius and soleus muscles were also all significantly increased in the FoxO TKO mice (FIG. 3B). The cross-sectional area of tibialis anterior muscle fibers in FoxO TKO mice was increased, to 180% of the control (FIG. 3C). This increased muscle fiber size may result from reduced protein degradation, because protein ubiquitination was significantly reduced in FoxO TKO muscles (FIG. 3D).

To delineate the role of FoxOs in denervation muscle atrophy, we examined denervation-dependent changes in the FoxO TKO mice. In both wild-type and FoxO TKO mice, denervation resulted in a time-dependent loss of muscle weight, with no change at 3 days but a significant reduction at 15 days after injury. However, denervation atrophy was attenuated 33% in FoxO TKO mice compared to wild-type controls (FIG. 3E). Muscle mass was preserved to approximately the same degree in the tibialis anterior, gastrocnemius and soleus muscles (FIG. 3F). Reductions in fiber cross-sectional area were similar to those in muscle weight (FIGS. 3G&H). Although the cross-sectional area of TKO muscle was significantly reduced following denervation, the cross-sectional area in that group was similar to that in the innervated wild-type muscle, because normally innervated FoxO TKO muscle was hypertrophic.

Denervation-induced protein ubiquitination was significantly reduced in FoxO TKO mice both in total and when normalized to total protein (FIGS. 3I and 3J). Denervation-induced expression of the genes encoding the E3 ubiquitin ligases atrogin and MuRF1 in FoxO TKO mice was similar to that in wild-type mice 3 days post-denervation, and was accompanied by a robust induction of the mRNA encoding myogenin at that time-point (FIG. 3K). However, the denervation-induced increase in mRNA abundance of atrogin and MuRF1 at 15 days post-denervation did not occur in FoxO TKO mice (FIG. 3L). At this time-point, the expression of the mRNAs encoding myogenin and HDAC4 were still significantly increased compared to pre-denervation amounts, but approximately 50% of that in wild-type denervated muscle. This suggests that FoxOs transcriptionally activate genes encoding E3 ubiquitin ligases only at later times after denervation, and that they could affect the HDAC-myogenin pathway to some degree, directly or indirectly.

Example 5

Inhibition of mTORC1 with Rapamycin Attenuates Denervation-Induced Skeletal Muscle Atrophy Because mTORC1 activation stimulates pathways similar to those activated by denervation, it was further investigated whether denervation-induced mTORC1 activity contributed to denervation muscle atrophy via suppression of Akt and activation of the Forkhead box O transcription factors (FoxOs).

In this context, mice with denervated hindlimbs were treated with rapamycin to decrease mTORC1 activity. Rapamycin treatment at the doses used did not influence body weight or innervated muscle weight (see Table 2) but significantly prevented both the reduction in cross-sectional area (FIG. 4A) and the muscle weight loss (FIG. 4B) that occurred following denervation. The denervation-induced expression of the genes encoding the E3 ubiquitin ligases atrogin and MuRF1 (FIG. 4C) and protein polyubiquitination (FIG. 4D) were also both significantly reduced by rapamycin treatment. However, denervation-induced expression of the gene encoding myogenin was not affected by rapamycin (FIG. 4E). This further supports the notion that myogenin was not involved in mTORC1-dependent regulation of muscle mass at the late stage of denervation. In contrast, rapamycin treatment rescued the denervation-suppressed phosphorylation of Akt (Thr$^{308}$) and FoxO1 (Ser$^{256}$) as well as inhibited the denervation-induced phosphorylation of S6 (FIG. 4F), suggesting that mTORC1 activity serves as an upstream regulator of Akt and FoxO in denervated muscle. These observations suggest that the inhibitory effect of rapamycin on denervation-induced atrophy is mediated by the normalization of the mTORC1-Akt-FoxO axis.

It was furthermore observed that the phosphorylation of the insulin receptor substrate 1 (IRS1) was increased in denervated muscle and was inhibited by rapamycin treatment (FIG. 4F). This is consistent with the observation that activation of the mTORC1 pathway leads to phosphorylation of IRS1 (in mouse, Ser$^{302}$ and Ser$^{307}$), resulting in the inhibition of the PI3K-Akt pathway (Sabatini et al., 2006; Zhang et al., 2008; Takano et al., 2001; Tremblay & Marette, 2001). Thus, phosphorylated IRS1 may mediate the cross-talk between the mTORC1-S6K pathway and the Akt-FoxO pathway and is linked to the reduction of phosphorylated Akt (Thr$^{308}$). In addition, the phosphorylation abundance of Akt-Ser473 (phosphorylated Akt-Ser473 over total Akt) was also reduced following denervation, but rapamycin treatment only showed a mild recue effect on this reduction, comparing to that of Akt-Thr308 (phosphorylated Akt-Thr308 over total Akt) (FIG. 4F). Although mTORC2 phosphorylates Akt at Ser473, the abundance of the mTORC2 components, mLST8 and rictor, were either increased or unchanged by denervation (FIG. 4F). Thus, the contribution of mTORC2 to the reduction of phosphorylated Akt-Ser473 in denervated muscle might be less compared to mTORC1. Taken together, denervation represses the phosphorylation of Akt (Thr308 and Ser473), and rapamycin treatment appears to rescue the phosphorylation of Akt mainly at Thr308 in denervated muscle.

Table 2 shows that the weight of innervated muscles does not change in response to rapamycin treatment.

TABLE 2

|    | Inn + Rapa | Inn + 1.5 | Inn + 6 |
| --- | --- | --- | --- |
| TA | 0.0705 | 0.0719 | 0.0686 |
|    | 0.0651 | 0.0697 | 0.0751 |
|    | 0.0642 | 0.068  | 0.0645 |
|    | 0.073  | 0.0898 | 0.078  |
|    | 0.0743 | 0.0795 | 0.0713 |
|    | 0.076  | 0.0597 | 0.0759 |

TABLE 2-continued

|  | | | |
|---|---|---|---|
| MEAN | 0.0705167 | 0.0731 | 0.0722333 |
| STDV | 0.0048947 | 0.0103771 | 0.0050753 |
| Ttest |  | 0.299077 | 0.2821019 |

|  | Inn + 0 | Inn + 1.5 | Inn + 6 |
|---|---|---|---|
| Gastroc | 0.1951 | 0.1984 | 0.2084 |
|  | 0.192 | 0.2043 | 0.2168 |
|  | 0.1837 | 0.2062 | 0.1798 |
|  | 196.4 | 212.6 | 210.1 |
|  | 178.4 | 167.3 | 217.7 |
|  | 249.7 | 196.7 | 230.5 |
| MEAN | 104.17847 | 96.201483 | 109.8175 |
| STDV | 116.30202 | 106.16093 | 120.25504 |
| Ttest |  | 0.4518632 | 0.4679141 |

|  | Inn + Rapa | Inn + 1.5 | Inn + 6 |
|---|---|---|---|
| sol | 0.0104 | 0.0114 | 0.0102 |
|  | 0.0085 | 0.0095 | 0.0116 |
|  | 0.0091 | 0.0099 | 0.0106 |
|  | 0.0102 | 0.0106 | 0.0106 |
|  | 0.0091 | 0.0102 | 0.0106 |
|  | 0.0108 | 0.0075 | 0.0115 |
| MEAN | 0.0096833 | 0.00985 | 0.01085 |
| STDV | 0.0009065 | 0.0013217 | 0.0005648 |
| Ttest |  | 0.4023777 | 0.0135025 |

|  | Rapa – 0 before | Rapa – 0 after | Rapa – 1.5 before | Rapa – 1.5 after | Rapa – 6 before | Rapa – 6 after |
|---|---|---|---|---|---|---|
| Body weight | 41 | 42 | 41 | 45 | 39 | 46 |
|  | 44 | 42 | 46 | 46 | 42 | 38 |
|  | 41 | 44 | 44 | 42 | 55 | 41 |
|  | 41 | 44 | 42 | 40 | 43 | 42 |
|  | 42 | 40 | 42 | 39 | 41 | 40 |
|  | 40 | 36 | 41 | 42 | 44 | 39 |
| MEAN | 41.5 | 41.333333 | 42.666667 | 42.333333 | 44 | 41 |
| STDV | 1.2583057 | 2.7487371 | 1.7950549 | 2.4944383 | 5.1639778 | 2.5819889 |
| Ttest |  | 0.4437322 |  | 0.3897577 |  | 0.1015511 |

Example 6

Attenuation/Prevention of Skeletal Muscle Atrophy by Rapamycin in Denervated Muscle Requires FoxO Although rapamycin treatment restored the phosphorylation of Akt and FoxO and reduced post-denervation atrophy, it was important to determine whether FoxO was required. The FoxO TKO model was not ideal to investigate this issue, because pre-denervation muscle hypertrophy in FoxO TKO mice could confound potential protective effects of rapamycin. Thus, a dominant negative form of FoxO was generated which lacked the transactivation domains of FoxO1 but retained the DNA binding domain (DBD) and a nuclear translocation signal (NLS) (FIG. 4H). In cultured cells, dominant-negative FoxO reversed the FoxO-induced activity of a FoxO-reporter gene (FIG. 4I). In addition, dominant-negative FoxO significantly reduced atrogin promoter activity in cultured myotubes (FIG. 4J). Denervated tibialis anterior muscles were then cultured which were electroporated with control or FoxO-DN plasmids and a GFP reporter plasmid in the presence or absence of rapamycin. Measurement of the cross-sectional area of the GFP-positive fibers demonstrated that the dominant-negative form of FoxO protected against denervation-induced muscle atrophy (FIG. 4G). Thus, blockage of FoxO after muscle denervation was effective in reducing muscle atrophy, indicating that pre-denervation induction of muscle hypertrophy was not required. Furthermore, although rapamycin treatment prevented the reduction in cross-sectional area following denervation in fibers electroporated with the control plasmid, rapamycin did not have an additional effect on fibers electroporated with the dominant-negative form of FoxO. This result suggests that the protective effect of rapamycin on denervated muscle is mediated through regulation of FoxO (FIG. 4G).

Example 7

Figure 5:
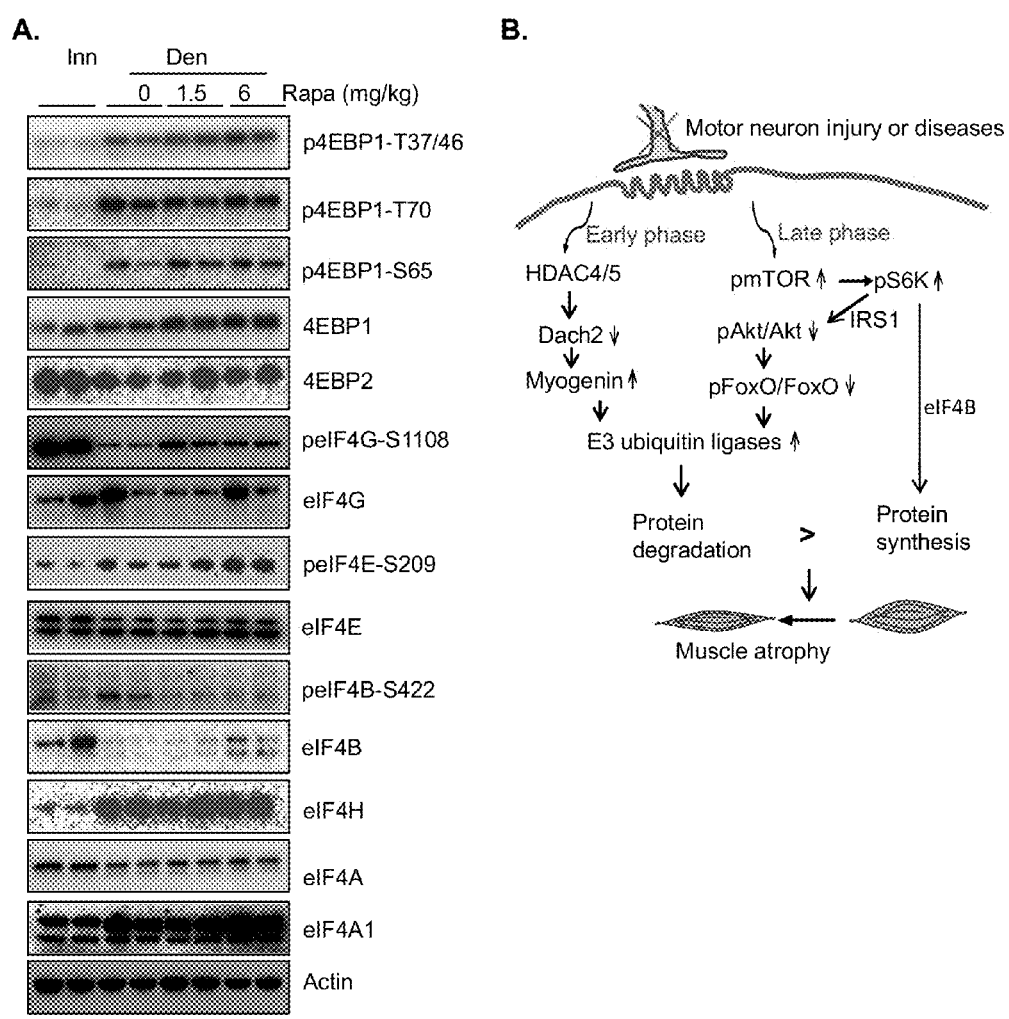
FIG. 5 illustrates that rapamycin-sensitive mTORC1 plays a lesser role in regulating protein synthesis in denervated muscle. A) Protein lysates from innervated and denervated gastrocnemius muscles from mice that received or did not receive rapamcyin treatment were immunoblotted for various translation initiation factors in the 4EBP and eIF4 families (n=2 randomly selected mice per treatment shown). B) Model for the temporal regulation of signaling cascades in neurogenic muscle atrophy. Denervation rapidly activates HDAC4 and 5, Dach2 and myogenin, which appears to trigger the early-phase induction of E3 ubiquitin ligases. Denervation later induces activation of FoxO through mTORC1-dependent inhibition of Akt, which appears to be responsible for the induction of E3 ubiquitin ligases at the later phase. Protein degradation induced by these early and late cascades after denervation is apparently more robust than protein synthesis, the net result being muscle atrophy.

The Role of Rapamycin-Sensitive mTORC1 in Regulating Protein Synthesis in Denervated Muscle Activated mTORC1 was demonstrated to induce protein degradation in denervated muscle, but it is unlikely that this is the sole function of activated mTORC1 in denervated muscle. mTORC1 induces protein synthesis by promoting the protein phosphorylation of regulators of eukaryotic translation initiation, including members of the 4EBP and eIF4 families. In contrast to the unchanged total protein abundance of 4EBP1, phosphorylation of several sites on 4EBP1 was increased, including $Thr^{37}$, $Thr^{46}$ and $Ser^{65}$ (FIG. 5A), suggesting that denervation could activate protein synthesis by triggering the phosphorylation of 4EBP1. Phosphorylated 4EBP1 dissociates from eIF4E and activates translation initiation (Gingras et al., 2001). However, none of these phosphorylation events were particularly sensitive to rapamycin treatment. Therefore, rapamycin-sensitive mTORC1 might not regulate the phosphorylation of 4EBP1 in denervated muscle. Similarly, phosphorylation of eIF4E and total protein abundance of eIF4H were increased in a rapamycin-insensitive manner in denervated muscle. In contrast, the increased phosphorylation of eIF4B at $Ser^{422}$ by denervation was reversed by rapamycin treatment (FIG. 5A). Denervation also resulted in suppression of phosphorylation of eIF4G, which was also partially recovered by rapamycin treatment (FIG. 5A). Phosphorylation of eIF4B at $Ser^{422}$ leads to enhanced interaction with eIF3, promoting protein translation (Shahbazian et al., 2006), and phosphorylation of eIF4G inhibits cap-dependent protein translation (Ling et al., 2005). Therefore, decreased phosphorylation of eIF4G and increased phosphorylation of eIF4B would be predicted to favor protein synthesis in denervated muscle. The normalization of these denervation-induced changes by rapamycin could compromise protein synthesis. However, the finding that other members in eIF4 families, as well as 4EBP1, show increased abundance after denervation, in a rapamycin-insensitive manner, suggests that rapamycin might have a limited effect in compromising protein synthesis in denervated muscle. This small atrophy-promoting effect of rapamycin appears to be overwhelmed by the atrophy-preventing effects delineated above.

Example 8

Attenuation/Prevention of Skeletal Muscle Atrophy in Denervated Muscle by Decreasing the Activity of FoxO 1, 3 and/or 4 Using a FoxO Fusion Protein By introducing TAT tags to one or both sides of the DNA binding domain of FoxO, human dominant negative FoxO-TAT fusion proteins are engineered that are capable of penetrating cell membranes in vitro and in vivo.

FIG. 6 illustrates a FoxO-TAT fusion protein with a TAT tag at the N-terminus (SEQ ID NO:1) and a FoxO-TAT fusion protein with a TAT tag at both the N-terminus and the C-terminus (SEQ ID NO:2).

The DNA binding domain of FoxO, which the inventors have shown to efficiently shut off the expression of the ubiquitin ligases, whose transcription is controlled by FoxO and which are critical to muscle protein degradation, is cloned and fused to a cell penetrating peptide sequence, such as a TAT tag, a 10-amino acid peptide, that has been shown to have cell penetrating ability in vitro and in vivo. This construct which is designated dominant negative FoxO, aka FoxO-DN, is then transformed into bacteria, the expression of the fusion protein is induced with isopropyl-beta-D-thiogalactopyranoside (IPTG), and the protein is purified via affinity chromatography. The FoxO-DN-TAT fusion proteins whose sequences are shown in FIG. 6, are capable of penetrating cell membranes in vitro and in vivo, and are capable of decreasing and shutting off the activity of all FoxO 1, 3 and 4 through competitive binding to the consensus DNA binding sequence of the Forkhead transcription factors.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

Aguilar, V., Alliouachene, S., Sotiropoulos, A., Sobering, A., Athea, Y., Djouadi, F., Miraux, S., Thiaudière, E., Foretz, M., Viollet, B., et al. (2007). S6 kinase deletion suppresses muscle growth adaptations to nutrient availability by activating AMP kinase. Cell Metab 5, 476-487.

Argadine, H. M., Mantilla, C. B., Zhan, W. Z., and Sieck, G. C. (2011). Intracellular signaling pathways regulating net protein balance following diaphragm muscle denervation. Am J Physiol Cell Physiol 300, C318-327.

Beehler, B. C., Sleph, P. G., Benmassaoud, L., and Grover, G. J. (2006). Reduction of skeletal muscle atrophy by a proteasome inhibitor in a rat model of denervation. Exp Biol Med (Maywood) 231, 335-341.

Bentzinger, C. F., Romanino, K., Cloëtta, D., Lin, S., Mascarenhas, J. B., Oliveri, F., Xia, J., Casanova, E., Costa, C. F., Brink, M., et al. (2008). Skeletal muscle-specific ablation of raptor, but not of rictor, causes metabolic changes and results in muscle dystrophy. Cell Metab 8, 411-424.

Bodine, S. C., Latres, E., Baumhueter, S., Lai, V. K., Nunez, L., Clarke, B. A., Poueymirou, W. T., Panaro, F. J., Na, E., Dharmarajan, K., et al. (2001a). Identification of ubiquitin ligases required for skeletal muscle atrophy. Science 294, 1704-1708.

Bodine, S. C., Stitt, T. N., Gonzalez, M., Kline, W. O., Stover, G. L., Bauerlein, R., Zlotchenko, E., Scrimgeour, A., Lawrence, J. C., Glass, D. J., et al. (2001b). Akt/mTOR pathway is a crucial regulator of skeletal muscle hypertrophy and can prevent muscle atrophy in vivo. Nat Cell Biol 3, 1014-1019.

Cho, S. J. (1998). Rational Combinatorial Library Design. 2. Rational Design of Targeted Combinatorial Peptide Libraries Using Chemical Similarity Probe and the Inverse QSAR Approaches. J Chem Inf Comput Sci 38 (2), pp 259-268.

Choo, A. Y. et al. (2008). Rapamycin differentially inhibits S6Ks and 4E-BP1 to mediate cell-type-specific repression of mRNA translation. PNAS 105, p. 17414-17419.

Cohen, T. J., Waddell, D. S., Barrientos, T., Lu, Z., Feng, G., Cox, G. A., Bodine, S. C., and Yao, T. P. (2007). The histone deacetylase HDAC4 connects neural activity to muscle transcriptional reprogramming. J Biol Chem 282, 33752-33759.

Gingras, A. C., Raught, B., Gygi, S. P., Niedzwiecka, A., Miron, M., Burley, S. K., Polakiewicz, R. D., Wyslouch-Cieszynska, A., Aebersold, R., and Sonenberg, N. (2001). Hierarchical phosphorylation of the translation inhibitor 4E-BP1. Genes Dev 15, 2852-2864.

Glickman, M. H. & Ciechanover, A. (2002). The ubiquitin-proteasome proteolytic pathway: destruction for the sake of construction. Physiol Rev 87:373-428.

Gomes, M. D., Lecker, S. H., Jagoe, R. T., Navon, A., and Goldberg, A. L. (2001). Atrogin-1, a muscle-specific F-box protein highly expressed during muscle atrophy. Proc Natl Acad Sci USA 98, 14440-14445.

Harrison, D. E., Strong, R., Sharp, Z. D., Nelson, J. F., Astle, C. M., Flurkey, K., Nadon, N. L., Wilkinson, J. E., Frenkel, K., Carter, C. S., et al. (2009). Rapamycin fed late in life extends lifespan in genetically heterogeneous mice. Nature 460, 392-395.

Hasty, P., Bradley, A., Morris, J. H., Edmondson, D. G., Venuti, J. M., Olson, E. N., and Klein, W. H. (1993).

Muscle deficiency and neonatal death in mice with a targeted mutation in the myogenin gene. Nature 364, 501-506.

Hay, N. and Sonenberg, N. (2004). Upstream and downstream of mTOR. Genes Dev 18(16), p. 1926-45.

Hosaka, T., Biggs, W. H., Tieu, D., Boyer, A. D., Varki, N. M., Cavenee, W. K., and Arden, K. C. (2004). Disruption of forkhead transcription factor (FOXO) family members in mice reveals their functional diversification. Proc Natl Acad Sci USA 101, 2975-2980.

Hsieh, A. C., Liu, Y., Edlind, M. P., Ingolia, N. T., Janes, M. R., Sher, A., Shi, E. Y., Stumpf, C. R., Christensen, C., Bonham, M. J., et al. (2012). The translational landscape of mTOR signalling steers cancer initiation and metastasis. Nature 485, 55-61.

Hsu, P. P., Kang, S. A., Rameseder, J., Zhang, Y., Ottina, K. A., Lim, D., Peterson, T. R., Choi, Y., Gray, N. S., Yaffe, M. B., et al. (2011). The mTOR-regulated phosphoproteome reveals a mechanism of mTORC1-mediated inhibition of growth factor signaling. Science 332, 1317-1322.

Hu, Y., Leung, H. B., Lu W. W., Luk K. D. (2006). Consequence of paraspinal muscle after spinal fusion: an experimental study. Stud Health Technol Inform 123:461-466.

Inoki, K., Mori, H., Wang, J., Suzuki, T., Hong, S., Yoshida, S., Blattner, S. M., Ikenoue, T., Rüegg, M. A., Hall, M. N., et al. (2011). mTORC1 activation in podocytes is a critical step in the development of diabetic nephropathy in mice. J Clin Invest 121, 2181-2196.

Jagoe, R. T., & Goldberg, A. L. (2001). What do we really know about the ubiquitin-proteasome pathway in muscle atrophy? Curr Opin Clin Nutr Metab Care 4:183-190.

Kamei, Y., Miura, S., Suzuki, M., Kai, Y., Mizukami, J., Taniguchi, T., Mochida, K., Hata, T., Matsuda, J., Aburatani, H., et al. (2004). Skeletal muscle FOXO1 (FKHR) transgenic mice have less skeletal muscle mass, down-regulated Type I (slow twitch/red muscle) fiber genes, and impaired glycemic control. J Biol Chem 279, 41114-41123.

Knapp, J. R., Davie, J. K., Myer, A., Meadows, E., Olson, E. N., and Klein, W. H. (2006). Loss of myogenin in postnatal life leads to normal skeletal muscle but reduced body size. Development 133, 601-610.

Lecker, S. H., Jagoe, R. T., Gilbert, A., Gomes, M., Baracos, V., Bailey, J., Price, S. R., Mitch, W. E., and Goldberg, A. L. (2004). Multiple types of skeletal muscle atrophy involve a common program of changes in gene expression. FASEB J 18, 39-51.

Lee, C. H., Inoki, K., and Guan, K. L. (2007). mTOR pathway as a target in tissue hypertrophy. Annu Rev Pharmacol Toxicol 47, 443-467.

Levine, S., Nguyen, T., Taylor, N., Friscia, M. E., Budak, M. T., Rothenberg, P., Zhu, J., Sachdeva, R., Sonnad, S., Kaiser, L. R., Rubinstein, N. A., Powers, S. K., Shrager, J. B. (2008). Rapid Disuse Atrophy of Diaphragm Fibers in Mechanically Ventilated Humans. N Engl J Med 358: 1327-1335.

Ling, J., Morley, S. J., and Traugh, J. A. (2005) Inhibition of cap-dependent translation via phosphorylation of eIF4G by protein kinase Pak2. EMBO J 24, 4094-4105.

Luff, A. R. (1998). Age-associated Changes in the Innervation of Muscle Fibers and Changes in the Mechanical Properties of Motor Units. Ann N Y Acad Sci. 1998 Nov. 20; 8540:92-101.

Machida, M., Takeda, K., Yokono, H., Ikemune, S., Taniguchi, Y., Kiyosawa, H., and Takemasa, T. (2012). Reduction of ribosome biogenesis with activation of the mTOR pathway in denervated atrophic muscle. J Cell Physiol 227, 1569-1576.

Macpherson, P. C., Wang, X., and Goldman, D. (2011). Myogenin regulates denervation-dependent muscle atrophy in mouse soleus muscle. J Cell Biochem 112, 2149-2159.

Meikle, L., McMullen, J. R., Sherwood, M. C., Lader, A. S., Walker, V., Chan, J. A., and Kwiatkowski, D. J. (2005). A mouse model of cardiac rhabdomyoma generated by loss of Tsc1 in ventricular myocytes. Hum Mol Genet 14, 429-435.

Mieulet, V., Roceri, M., Espeillac, C., Sotiropoulos, A., Ohanna, M., Oorschot, V., Klumperman, J., Sandri, M., and Pende, M. (2007). S6 kinase inactivation impairs growth and translational target phosphorylation in muscle cells maintaining proper regulation of protein turnover. Am J Physiol Cell Physiol 293, C712-722.

Moresi, V., Williams, A. H., Meadows, E., Flynn, J. M., Potthoff, M. J., McAnally, J., Shelton, J. M., Backs, J., Klein, W. H., Richardson, J. A., et al. (2010). Myogenin and class II HDACs control neurogenic muscle atrophy by inducing E3 ubiquitin ligases. Cell 143, 35-45.

Nabeshima, Y., Hanaoka, K., Hayasaka, M., Esumi, E., Li, S., and Nonaka, I. (1993). Myogenin gene disruption results in perinatal lethality because of severe muscle defect. Nature 364, 532-535.

Paik, J. H., Kollipara, R., Chu, G., Ji, H., Xiao, Y., Ding, Z., Miao, L., Tothova, Z., Horner, J. W., Carrasco, D. R., et al. (2007). FoxOs are lineage-restricted redundant tumor suppressors and regulate endothelial cell homeostasis. Cell 128, 309-323.

Proud, C. G. (2009). mTORC1 signalling and mRNA translation. Biochem Soc Trans 37(Pt 1), p. 227-31.

Reed, S. A., Sandesara, P. B., Senf, S. M., and Judge, A. R. (2011). Inhibition of FoxO transcriptional activity prevents muscle fiber atrophy during cachexia and induces hypertrophy. FASEB J.

Sabatini, D. M. (2006). mTOR and cancer: insights into a complex relationship. Nat Rev Cancer 6, 729-734.

Sandri, M., Sandri, C., Gilbert, A., Skurk, C., Calabria, E., Picard, A., Walsh, K., Schiaffino, S., Lecker, S. H., and Goldberg, A. L. (2004). Foxo transcription factors induce the atrophy-related ubiquitin ligase atrogin-1 and cause skeletal muscle atrophy. Cell 117, 399-412.

Senf, S. M., Dodd, S. L., and Judge, A. R. (2010). FOXO signaling is required for disuse muscle atrophy and is directly regulated by Hsp70. Am J Physiol Cell Physiol 298, C38-45.

Serini, G., et al. (1998). The fibronectin domain ED-A is crucial for myofibroblastic phenotype induction by transforming growth factor-beta1. J Cell Biol 142(3), p. 873-81.

Shahbazian, D., Roux, P. P., Mieulet, V., Cohen, M. S., Raught, B., Taunton, J., Hershey, J. W., Blenis, J., Pende, M., and Sonenberg, N. (2006). The mTOR/PI3K and MAPK pathways converge on eIF4B to control its phosphorylation and activity. EMBO J 25, 2781-2791.

Stitt, T. N., Drujan, D., Clarke, B. A., Panaro, F., Timofeyva, Y., Kline, W. O., Gonzalez, M., Yancopoulos, G. D., and Glass, D. J. (2004). The IGF-1/PI3K/Akt pathway prevents expression of muscle atrophy-induced ubiquitin ligases by inhibiting FOXO transcription factors. Mol Cell 14, 395-403.

Sun, X (1998). Exploiting Incommensurate Symmetry Numbers: Rational Design and Assembly of $M_2M_3'L_6$ Supramolecular Clusters with $C_{3h}$ Symmetry. Angewandte Chemie 38 (9), p. 1303-1307.

Takano, A., Usui, I., Haruta, T., Kawahara, J., Uno, T., Iwata, M., and Kobayashi, M. (2001). Mammalian target of rapamycin pathway regulates insulin signaling via subcellular redistribution of insulin receptor substrate 1 and integrates nutritional signals and metabolic signals of insulin. Mol Cell Biol 21, 5050-5062.

Tang, H., and Goldman, D. (2006). Activity-dependent gene regulation in skeletal muscle is mediated by a histone deacetylase (HDAC)-Dach2-myogenin signal transduction cascade. Proc Natl Acad Sci USA 103, 16977-16982.

Tang, H., Macpherson, P., Marvin, M., Meadows, E., Klein, W. H., Yang, X. J., and Goldman, D. (2009). A histone deacetylase 4/myogenin positive feedback loop coordinates denervation-dependent gene induction and suppression. Mol Biol Cell 20, 1120-1131.

Thoreen, C. C., Chantranupong, L., Keys, H. R., Wang, T., Gray, N. S., and Sabatini, D. M. (2012). A unifying model for mTORC1-mediated regulation of mRNA translation. Nature 485, 109-113.

Tremblay, F., and Marette, A. (2001). Amino acid and insulin signaling via the mTOR/p70 S6 kinase pathway. A negative feedback mechanism leading to insulin resistance in skeletal muscle cells. J Biol Chem 276, 38052-38060.

Uhlmann, E. J., Wong, M., Baldwin, R. L., Bajenaru, M. L., Onda, H., Kwiatkowski, D. J., Yamada, K., and Gutmann, D. H. (2002). Astrocyte-specific TSC1 conditional knockout mice exhibit abnormal neuronal organization and seizures. Ann Neurol 52, 285-296.

Wan, M., Wu, X., Guan, K. L., Han, M., Zhuang, Y., and Xu, T. (2006). Muscle atrophy in transgenic mice expressing a human TSC1 transgene. FEBS Lett 580, 5621-5627.

Wang, X., and Proud, G. G. (2006). The mTOR pathway in the control of protein synthesis. Physiology 21, 362-369.

Yu, Y., Yoon, S. O., Poulogiannis, G., Yang, Q., Ma, X. M., Villén, J., Kubica, N., Hoffman, G. R., Cantley, L. C., Gygi, S. P., et al. (2011). Phosphoproteomic analysis identifies Grb10 as an mTORC1 substrate that negatively regulates insulin signaling. Science 332, 1322-1326.

Zhang, J., Gao, Z., Yin, J., Quon, M. J., and Ye, J. (2008). S6K directly phosphorylates IRS-1 on Ser-270 to promote insulin resistance in response to TNF-(alpha) signaling through IKK2. J Biol Chem 283, 35375-35382.

Zhang, X., Li, L., Chen, S., Yang, D., Wang, Y., Wang, Z., and Le, W. (2011). Rapamycin treatment augments motor neuron degeneration in SOD1(G93A) mouse model of amyotrophic lateral sclerosis. Autophagy 7, 412-425.

---

What is claimed is:

1. A method of attenuating denervation-induced skeletal muscle atrophy in a mammalian subject, comprising administering to said subject suffering from denervation-induced skeletal muscle atrophy a composition comprising an agent that decreases activity of mammalian target of rapamycin complex 1 in a dosage and dosing regimen effective to attenuate denervation-induced skeletal muscle atrophy in said subject.

2. The method in accordance to claim 1, wherein said denervation-induced muscle atrophy results from sarcopenia.

3. A method of preventing denervation-induced skeletal muscle atrophy in a mammalian subject, comprising administering to said subject being at risk of developing a denervation-induced skeletal muscle atrophy a composition comprising an agent that decreases activity of mammalian target of rapamycin complex 1 in a dosage and dosing regimen effective to prevent denervation-induced skeletal muscle atrophy in said subject.

4. The method in accordance to claim 3, wherein said denervation-induced muscle atrophy results from sarcopenia.

5. A method of attenuating skeletal muscle atrophy in a mammalian subject, comprising administering to said subject suffering from denervation-induced skeletal muscle atrophy a composition comprising an agent that comprises a sequence that is substantially identical to SEQ NO ID 2 in a dosage and dosing regimen effective to attenuate denervation-induced skeletal muscle atrophy in said subject.

6. The method in accordance to claim 5, wherein said muscle atrophy results from sarcopenia.

7. The method according to claim 5, further comprising administering to said subject a composition comprising an agent that blocks mTOR complex 1 activity.

8. A method of preventing denervation-induced skeletal muscle atrophy in a mammalian subject, comprising administering to said subject being at risk of developing a denervation-induced skeletal muscle atrophy a composition comprising an agent that comprises a sequence that is substantially identical to SEQ NO ID 2 in a dosage and dosing regimen effective to prevent denervation-induced skeletal muscle atrophy.

9. The method in accordance to claim 8, wherein said denervation-induced muscle atrophy results from sarcopenia.

10. The method according to claim 8, further comprising administering to said subject a composition comprising an agent that blocks mTOR complex 1 activity.

11. The method according to any of claim 1, 2, 3, 4, 7, or 10 wherein the agent is rapamycin or an analog of rapamycin.

* * * * *